United States Patent
Inada et al.

(10) Patent No.: US 10,393,730 B2
(45) Date of Patent: Aug. 27, 2019

(54) ENERGY MALNUTRITION EVALUATION FOR LIVER DISEASE TEST SUBJECT

(71) Applicant: OTSUKA PHARMACEUTICAL CO., LTD., Tokyo (JP)

(72) Inventors: Makoto Inada, Osaka (JP); Jun-ichi Kunizaki, Osaka (JP); Kazuki Tobita, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 257 days.

(21) Appl. No.: 15/324,486

(22) PCT Filed: Jul. 7, 2015

(86) PCT No.: PCT/JP2015/069511
§ 371 (c)(1),
(2) Date: Jan. 6, 2017

(87) PCT Pub. No.: WO2016/006601
PCT Pub. Date: Jan. 14, 2016

(65) Prior Publication Data
US 2017/0199172 A1    Jul. 13, 2017

(30) Foreign Application Priority Data
Jul. 9, 2014    (JP) .................................. 2014-141751

(51) Int. Cl.
*G01N 33/497*    (2006.01)
*A61B 5/00*    (2006.01)
(Continued)

(52) U.S. Cl.
CPC .......... *G01N 33/497* (2013.01); *A61B 5/082* (2013.01); *A61B 5/083* (2013.01); *A61B 5/0836* (2013.01);
(Continued)

(58) Field of Classification Search
CPC ....... A61B 5/0813; A61B 5/082; A61B 5/083; A61B 5/0836; A61B 5/14532;
(Continued)

(56) References Cited

U.S. PATENT DOCUMENTS

| 6,186,958 B1 * | 2/2001 | Katzman | A61B 5/0836 |
| | | | 128/898 |
| 2005/0147560 A1 * | 7/2005 | Yatscoff | A61B 5/0813 |
| | | | 424/9.1 |

(Continued)

FOREIGN PATENT DOCUMENTS

| JP | 2002-513911 A | 5/2002 |
| JP | 2011-026314 A | 2/2011 |

(Continued)

OTHER PUBLICATIONS

Miwa, Yoshiyuki et al., "Liver cirrhosis and indirect calorimetry," Japanese Journal of Nutritional Assessment, 2003, vol. 20, No. 4, pp. 47-50.

(Continued)

*Primary Examiner* — Jennifer Wecker
(74) *Attorney, Agent, or Firm* — Sughrue Mion, PLLC

(57) ABSTRACT

A method for measuring energy malnutrition in a liver disease test subject, a method for determining whether a liver disease test subject is in an energy malnutrition state, a method for determining the necessity of nutrition therapy for a liver disease test subject having energy malnutrition, a composition usable in these methods, and the like are provided. The method for measuring energy malnutrition in a liver disease test subject includes the steps of collecting expired air containing labeled carbon dioxide that is generated in the body of a liver disease test subject by being converted from a composition containing, as an active ingredient, glucose labeled with at least one isotope C; and determining the ratio of labeled $CO_2$ amount to unlabeled (Continued)

$CO_2$ amount, or the ratio of labeled $CO_2$ amount to total $CO_2$ amount in expired air.

21 Claims, 4 Drawing Sheets

(51) Int. Cl.
*A61B 5/08* (2006.01)
*A61B 5/083* (2006.01)
*A61B 5/145* (2006.01)

(52) U.S. Cl.
CPC ........ *A61B 5/14532* (2013.01); *A61B 5/4244* (2013.01); *A61B 5/4836* (2013.01); *A61B 5/7275* (2013.01); *A61B 5/0813* (2013.01); *G01N 2458/15* (2013.01); *G01N 2800/02* (2013.01); *G01N 2800/085* (2013.01); *G01N 2800/52* (2013.01)

(58) Field of Classification Search
CPC ... A61B 5/4244; A61B 5/4836; A61B 5/7275; G01N 2458/15; G01N 2800/02; G01N 2800/085; G01N 2800/52; G01N 33/497; G06F 19/00
See application file for complete search history.

(56) References Cited

U.S. PATENT DOCUMENTS

| | | |
|---|---|---|
| 2012/0116069 A1 | 5/2012 | Iwasaki et al. |
| 2012/0197622 A1* | 8/2012 | Jain ..................... G06F 19/3418 703/11 |
| 2014/0033795 A1* | 2/2014 | Guggenheim ......... A61B 5/082 73/23.3 |
| 2015/0204852 A1 | 7/2015 | Inada et al. |
| 2016/0146791 A1* | 5/2016 | Inada ................... A61B 5/0836 436/133 |

FOREIGN PATENT DOCUMENTS

| | | |
|---|---|---|
| WO | 99/056790 A2 | 11/1999 |
| WO | 99/056790 A3 | 11/1999 |
| WO | 2014/030650 A1 | 2/2014 |

OTHER PUBLICATIONS

Habu, Daiki, "Kankohen no Byotai to To Taisha Ijo tono Kanrensei", CDEJ news Letter, Apr. 2010, vol. 26, p. 10.

"Liver Cirrhosis Practice Guideline", P.Xix, 2010, Edited by The Japanese Society of Gastroenterology, Published by Nankodo, (total 2 pages).

Nakaya, Yutaka et al., "BCAA-enriched snack improves nutritional state of cirrhosis", Nutrition, 2007, vol. 23, pp. 113-120.

International Preliminary Report on Patentability with Written Opinion dated Jan. 10, 2017, issued by the International Searching Authority in Application No. PCT/JP2015/069511.

International Search Report dated Sep. 1, 2015, issued by the International Searching Authority in Application No. PCT/JP2015/069511.

* cited by examiner

ENERGY MALNUTRITION EVALUATION FOR LIVER DISEASE TEST SUBJECT

CROSS REFERENCE TO RELATED APPLICATIONS

This is a National Stage of International Application No. PCT/JP2015/069511 filed Jul. 7, 2015, claiming priority based on Japanese Patent Application No. 2014-141751 filed Jul. 9, 2014, the contents of all of which are incorporated herein by reference in their entirety.

TECHNICAL FIELD

The present invention relates to a method for measuring energy malnutrition in a liver disease test subject, a method for determining whether a liver disease test subject is in an energy malnutrition state, a method for determining the necessity of nutrition therapy for a liver disease test subject having energy malnutrition, and a composition for use in these methods.

BACKGROUND ART

It is known that liver cirrhosis patients often have protein-energy malnutrition (PEM). Protein malnutrition has been evaluated based on serum albumin value. When the value is 3.5 g/dl or less, the subject is determined to be in a protein malnutrition state (Non-patent Document 1). Further, energy malnutrition is evaluated based on the respiratory quotient obtained from indirect calorimetry. When the value (non-protein respiratory quotient) is less than 0.85, the subject is determined to be in an energy malnutrition state. It is reported that 70% of liver cirrhosis patients are in a protein malnutrition state, 62% of them are in an energy malnutrition state, and 50% of them have a combined symptom of protein malnutrition and energy malnutrition (i.e., PEM).

Of these patients with malnutrition, liver cirrhosis patients in an energy malnutrition state are known to fall into a kind of starvation state, even if they have ordinary meals. This particularly occurs when there is a long interval between the meals. This type of phenomenon typically occurs at night, i.e., due to the long interval between dinner and breakfast the next day. It is said that liver cirrhosis patients may fall into a starvation state, even within one night, to an extent equivalent to that of a healthy subject who has fasted for three days. Since energy malnutrition greatly influences prognosis or quality of life, it is important to perform an appropriate diet therapy to alleviate the starvation state. For example, a common technique has been late-evening snacking (LES), in which the patients have a small amount of meal before bedtime so as to avoid energy shortage in the liver at night (Non-patent Document 2).

On the other hand, such diet therapies, in particular, late-evening snacking, increase meal frequency; moreover, since late-evening snacking allows the patients to have a meal before bedtime, there is a risk of obesity due to extra calories. Further, particularly for patients with diabetes, borderline diabetes, insulin resistance, obesity, or the like, it is desirable to consider performing late-evening snacking or similar treatments in consideration of these diseases. Therefore, in diet therapy for liver cirrhosis patients, it is desirable to understand the presence or absence of the energy malnutrition state of the liver cirrhosis patients, while also considering the presence or absence of other diseases such as diabetes, borderline diabetes, insulin resistance, and the like.

As described above, energy malnutrition has previously been evaluated using, as an index, the respiratory quotient obtained from indirect calorimetry. In this method, the metabolic states of the nutrient factors in the body have been indirectly evaluated using a volume ratio of carbon dioxide excretion amount to oxygen consumption amount upon energy conversion. However, indirect calorimetry is expensive, requires a special device, and is only performed in limited institution. Therefore, currently, indirect calorimetry is applied to only a limited number of patients. Further, to ensure accurate measurement and calculation of the respiratory quotient, the measurement of indirect calorimetry usually takes at least two hours. During the measurement, the patients must be kept quiet in bed, and prevented from falling asleep. Therefore, in order to ensure that the measurement is performed under appropriate conditions, monitoring by an observer or the like is necessary. This causes pain to and burdens both the patient and the observer. Further, as described above, since the evaluation by indirect calorimetry is indirect evaluation based on the respiratory quotient determined by calculation, it is unclear what nutrient factor actually combusted. If the presence or absence, or the extent of the energy malnutrition state is unclear, it is difficult to perform an appropriately diet therapy. Further, in the case where execution of diet therapy for an energy malnutrition state must be determined in consideration of the presence or absence of other diseases such as diabetes, if the evaluation of energy malnutrition is difficult and troublesome, it may further hinder an appropriate treatment. Moreover, prolonged multiple tests increase the burden of the patient.

Therefore, it is important to easily and rapidly determine an energy malnutrition state of a liver disease subject, for example, a liver cirrhosis patient and a liver disease subject having a pre-liver cirrhosis condition, such as non-alcoholic fatty liver disease (NAFLD) or non-alcoholic steatohepatitis (NASH). It is also important to perform an appropriate diet therapy in consideration of the presence or absence of other diseases, such as diabetes, borderline diabetes, insulin resistance and the like.

CITATION LIST

Non-Patent Documents

Non-patent Document 1: Liver Cirrhosis Practice Guideline, Flow Chart (*Eiyo Ryoho* [Nutrition Therapy]), P. Xix, 2010, edited by The Japanese Society of Gastroenterology, published by Nankodo Non-patent Document 2: Nakaya, Y. et al., BCAA-enriched snack improves nutritional state of cirrhosis, Nutrition, Vol. 23, p. 113-120, 2007

SUMMARY OF INVENTION

Technical Problem

An object of the present invention is to provide a method for easily and rapidly measuring energy malnutrition in a liver disease test subject, and a method for easily and rapidly determining whether a liver disease test subject is in an energy malnutrition state. Further, another object of the present invention is to provide a method for easily and rapidly determining the necessity of nutrition therapy for a liver disease test subject having energy malnutrition, and a composition usable in these methods.

Solution to Problem

The present inventors conducted extensive research to achieve the above objects, and found that energy malnutrition in a liver disease test subject can be easily and rapidly measured based on the behavior of labeled carbon dioxide ($CO_2$) in expired air collected after administration of glucose labeled with isotope C, in particular, from the behavior of the abundance of carbon dioxide contained in expired air (the ratio of labeled $CO_2$ amount to unlabeled $CO_2$ amount, or the ratio of labeled $CO_2$ amount to total $CO_2$ amount). The present inventors further found that it is possible to easily and rapidly perform a judgment as to whether a liver disease test subject is in an energy malnutrition state as well as determination of the necessity of nutrition therapy for a liver disease test subject having energy malnutrition based on the results of such a measurement. The present inventors further found that it is possible to easily, rapidly, and more accurately determine the necessity of nutrition therapy for energy malnutrition by combining the above measurement results and the measurement results regarding other diseases such as diabetes, borderline diabetes, insulin resistance, and the like. The present invention has been accomplished by further consideration based on these findings, and includes the following inventions.

(1) Method for Measuring Energy Malnutrition in Liver Disease Test Subject

Item 1-1. A method for measuring energy malnutrition in a liver disease test subject, comprising steps (1-a) and (1-b) below:

(1-a) collecting expired air containing labeled carbon dioxide that is generated in the body of a liver disease test subject by being converted from a composition containing, as an active ingredient, glucose labeled with at least one isotope C; and (1-b) determining the ratio of labeled $CO_2$ amount to unlabeled $CO_2$ amount, or the ratio of labeled $CO_2$ amount to total $CO_2$ amount in expired air.

Item 1-2. A method for measuring energy malnutrition in a liver disease test subject, comprising step (1-ab) below:

(1-ab) determining the ratio of labeled $CO_2$ amount to unlabeled $CO_2$ amount, or the ratio of labeled $CO_2$ amount to total $CO_2$ amount in collected expired air, the expired air being excreted from the body of a liver disease test subject and containing labeled carbon dioxide that is generated in the body by being converted from a composition containing, as an active ingredient, glucose labeled with at least one isotope C.

Item 1-3. The method according to Item 1-1 or 1-2, further comprising step (1-c) below:

(1-c) comparing "the ratio of labeled $CO_2$ amount to unlabeled $CO_2$ amount, or the ratio of labeled $CO_2$ amount to total $CO_2$ amount in expired air" obtained in step (1-b) or (1-ab) (subject value) with "the ratio of labeled $CO_2$ amount to unlabeled $CO_2$ amount, or the ratio of labeled $CO_2$ amount to total $CO_2$ amount in expired air" in healthy subject (control value), thereby determining whether the subject value is lower than the control value.

Item 1-4. The method according to any one of Items 1-1 to 1-3, wherein the liver disease test subject is a liver cirrhosis test subject.

Item 1-5. The method according to any one of Items 1-1 to 1-4, wherein the liver disease test subject does not have a disease that may be worsened in symptom by a diet therapy for energy malnutrition (for example, at least one disease selected from the group consisting of diabetes, borderline diabetes, and insulin resistance).

Item 1-6. The method according to any one of Items 1-1 to 1-4, wherein the liver disease test subject also has diabetes.

Item 1-7. The method according to any one of Items 1-1 to 1-6, wherein the expired air is collected from a liver disease test subject in a fasting state.

Item 1-8. The method according to any one of Items 1-1 to 1-7, wherein the isotope C is $^{13}C$.

(2) Method for Determining Whether Liver Disease Test Subject is in an Energy Malnutrition State Item 2-1. A method for determining whether a liver disease test subject is in an energy malnutrition state, comprising steps (2-a) and (2-b) below:

(2-a) administering, to a liver disease test subject, a composition containing, as an active ingredient, glucose labeled with at least one isotope C that is converted in the body into labeled carbon dioxide and excreted in expired air, and collecting the expired air; and (2-b) determining the ratio of labeled $CO_2$ amount to unlabeled $CO_2$ amount, or the ratio of labeled $CO_2$ amount to total $CO_2$ amount in the expired air.

Item 2-2. The method according to Item 2-1, further comprising step (2-c) below:

(2-c) comparing "the ratio of labeled $CO_2$ amount to unlabeled $CO_2$ amount, or the ratio of labeled $CO_2$ amount to total $CO_2$ amount in expired air" in the test subject (subject value) obtained in step (2-b) with "the ratio of labeled $CO_2$ amount to unlabeled $CO_2$ amount, or the ratio of labeled $CO_2$ amount to total $CO_2$ amount in expired air" in healthy subject (control value), and determining that the test subject is in an energy malnutrition state when the subject value is lower than the control value, and determining that the test subject is not in an energy malnutrition state when the subject value is equal to or higher than the control value.

Item 2-3. The method according to Item 2-1 or 2-2, further comprising step (2-d) below:

(2-d) excluding one or more test subjects having a disease that may be worsened in symptom by a diet therapy for energy malnutrition (for example, at least one disease selected from the group consisting of diabetes, borderline diabetes and insulin resistance) from liver disease test subjects before step (2-a), or excluding one or more test subjects having a disease that may be worsened in symptom by a diet therapy for energy malnutrition (for example, at least one disease selected from the group consisting of diabetes, borderline diabetes and insulin resistance) from liver disease test subjects determined to have an energy malnutrition state in step (2-c).

Item 2-4. The method according to any one of Items 2-1 to 2-3, further comprising step (2-e) below:

(2-e) determining whether the liver disease test subject is a test subject having a disease that may be worsened in symptom by a diet therapy for energy malnutrition (for example, at least one disease selected from the group consisting of diabetes, borderline diabetes and insulin resistance) before the exclusion in step (2-d).

Item 2-5. The method according to any one of Items 2-1 to 2-4, wherein the liver disease test subject is a liver cirrhosis test subject.

Item 2-6. The method according to any one of Items 2-1 to 2-5, wherein the liver disease test subject also has diabetes.

Item 2-7. The method according to any one of Items 2-1 to 2-6, wherein step (2-a) is performed with a liver disease test subject in a fasting state.

Item 2-8. The method according to any one of Items 2-1 to 2-7, wherein the isotope C is $^{13}C$.

(3) Method for Determining the Necessity of Nutrition Therapy for Liver Disease Test Subject Having Energy Malnutrition Item 3-1. A method for determining the necessity of a nutrition therapy for a liver disease test subject having energy malnutrition, comprising steps (3-a) to (3-c) below:

(3-a) collecting expired air containing labeled carbon dioxide that is generated in the body of a liver disease test subject by being converted from a composition containing, as an active ingredient, glucose labeled with at least one isotope C;

(3-b) determining the ratio of labeled $CO_2$ amount to unlabeled $CO_2$ amount, or the ratio of labeled $CO_2$ amount to total $CO_2$ amount in the expired air; and (3-c) comparing "the ratio of labeled $CO_2$ amount to unlabeled $CO_2$ amount, or the ratio of labeled $CO_2$ amount to total $CO_2$ amount in the expired air" obtained in step (3-b) (subject value) with "the ratio of labeled $CO_2$ amount to unlabeled $CO_2$ amount, or the ratio of labeled $CO_2$ amount to total $CO_2$ amount in the expired air" in healthy subject (control value), thereby determining whether the subject value is lower than the control value.

Item 3-2. A method for determining the necessity of a nutrition therapy for a liver disease test subject having energy malnutrition, comprising steps (3-ab) and (3-c) below:

(3-ab) determining the ratio of labeled $CO_2$ amount to unlabeled $CO_2$ amount, or the ratio of labeled $CO_2$ amount to total $CO_2$ amount in expired air, the expired air being excreted from the body of a liver disease test subject and containing labeled carbon dioxide that is generated in the body by being converted from a composition containing, as an active ingredient, glucose labeled with at least one isotope C; and (3-c) comparing "the ratio of labeled $CO_2$ amount to unlabeled $CO_2$ amount, or the ratio of labeled $CO_2$ amount to total $CO_2$ amount in the expired air" obtained in step (3-ab) (subject value) with "the ratio of labeled $CO_2$ amount to unlabeled $CO_2$ amount, or the ratio of labeled $CO_2$ amount to total $CO_2$ amount in the expired air" in healthy subject (control value), thereby determining whether the subject value is lower than the control value.

Item 3-3. The method according to Item 3-1 or 3-2, further comprising step (3-d) below:

(3-d) excluding one or more test subject having a disease that may be worsened in symptom by a diet therapy for energy malnutrition (at least one disease selected from the group consisting of diabetes, borderline diabetes, and insulin resistance) from liver disease test subjects before step (3-a) or step (3-ab), or excluding one or more test subjects having a disease that may be worsened in symptom by a diet therapy for energy malnutrition (at least one disease selected from the group consisting of diabetes, borderline diabetes and insulin resistance) from liver disease test subjects determined to have a subject value lower than the control value in step (3-c).

Item 3-4. The method according to any one of Items 3-1 to 3-3, further comprising step (3-e) below:

(3-e) determining whether the liver disease test subject is a test subject having a disease that may be worsened in symptom by a diet therapy for energy malnutrition (at least one disease selected from the group consisting of diabetes, borderline diabetes, and insulin resistance) before the exclusion in step (3-d).

Item 3-5. The method according to any one of Items 3-1 to 3-4, wherein the liver disease test subject is a liver cirrhosis test subject.

Item 3-6. The method according to any one of Items 3-1 to 3-5, wherein the liver disease test subject also has diabetes.

Item 3-7. The method according to any one of Items 3-1 to 3-6, wherein the expired air is collected from a liver disease test subject in a fasting state.

Item 3-8. The method according to any one of Items 3-1 to 3-7 wherein the isotope C is $^{13}C$.

(4) Composition for Energy Malnutrition Measurement

Item 4-1. A composition for measuring energy malnutrition, the composition being used to be administered to a liver disease test subject and containing, as an active ingredient, glucose labeled with at least one isotope C that is converted into labeled carbon dioxide in the body and excreted in expired air.

Item 4-2. The composition for measuring energy malnutrition according to Item 4-1, wherein the isotope is $^{13}C$.

Item 4-3. The composition for measuring energy malnutrition according to Item 4-1 or 4-2, wherein the composition is used for determining whether the liver disease test subject is in an energy malnutrition state.

Item 4-4. The composition for measuring energy malnutrition according to any one of Items 4-1 to 4-3, wherein the composition is used for determining the necessity of a nutrition therapy for a liver disease test subject having energy malnutrition.

(5) Use of Labeled C-glucose

Item 5-1. Use of a composition for measuring energy malnutrition in a liver disease test subject, the composition comprising glucose labeled with at least one isotope C that is converted into labeled carbon dioxide in the body and excreted in expired air.

Item 5-2. The use according to Item 5-1, wherein the measurement of energy malnutrition in a liver disease test subject is performed by the method according to any one of Items 1-1 to 1-8.

Item 5-3. Use of a composition for determining whether a liver disease test subject is in an energy malnutrition state, the composition comprising glucose labeled with at least one isotope C that is converted into labeled carbon dioxide in the body and excreted in expired air.

Item 5-4. The use according to Item 5-3, wherein the determination as to whether a test subject is in an energy malnutrition state is performed by the method according to any one of Items 2-1 to 2-8.

Item 5-5. Use of a composition for determining the necessity of a nutrition therapy for a liver disease test subject having energy malnutrition, the composition comprising glucose labeled with at least one isotope C that is converted into labeled carbon dioxide in the body and excreted in expired air.

Item 5-6. The use according to Item 5-5, wherein the determination of necessity of a nutrition therapy for energy malnutrition is performed by the method according to any one of Items 3-1 to 3-8.

Advantageous Effects of Invention

The method of the present invention enables easy and rapid measurement of energy malnutrition of a liver disease test subject. Further, the method of the present invention further enables easy and rapid determination and evaluation of an energy malnutrition state of a liver disease test subject based on the measurement result. In particular, the present invention enables highly accurate determination and evaluation of an energy malnutrition state of a liver disease test subject, while reducing drawbacks, such as physical or mental pain of the liver disease test subject. Therefore, the present invention is useful as a replacement for the previously known respiratory quotient measurement.

Further, the method of the present invention enables easy and rapid determination of the necessity of nutrition therapy for energy malnutrition with high accuracy. Further, the method of the present invention enables easy and rapid determination of the necessity of intervention of nutrition therapy for energy malnutrition with high accuracy, while considering other diseases such as diabetes, borderline diabetes, insulin resistance, and the like.

Figure 1:
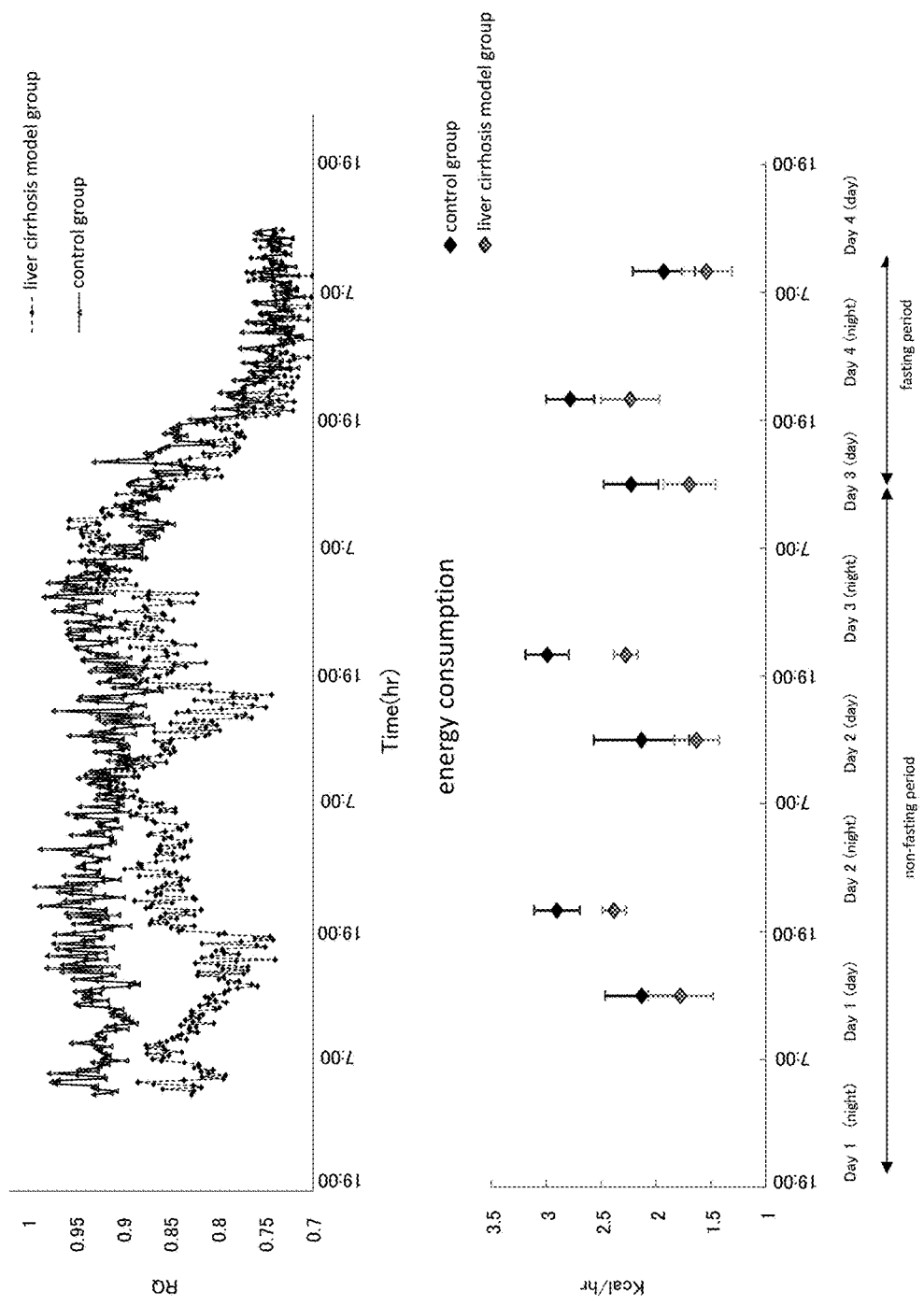
FIG. 1 shows results of measurement of respiratory quotient and energy consumption in a control group and a liver cirrhosis model group.

DESCRIPTION OF EMBODIMENTS (I) Explanation of Terms and Analysis Methods Regarding Labeled C-Glucose Breath Test The method of the present invention is based on using a labeled C-breath test, such as a $^{13}$C-breath test. Thus, before explaining the present invention, terms and analysis methods relating to a labeled C-breath test are described. In this explanation, $^{13}$C is used as an example of "isotope C" used in the present invention.

(I-1) $\delta^{13}$C Value (‰)

Abundances of isotopes are expressed in terms of isotopic ratio (R) in which the most abundant isotope of the same element is used as the denominator. Thus, with respect to carbon-13 ($^{13}$C), R value is expressed by the following formula in which carbon-12 ($^{12}$C) is used as the denominator.

$$R = {}^{13}C/{}^{12}C \quad \text{(Formula 1)}$$

Since R is a very small numerical value, it is difficult to directly measure. When a mass spectrometer is used for more accurate quantification, comparison with a standard substance is always performed. The measurement result is represented by $\delta 60$ value defined by the following formula.

$$\delta^{13}C = ([R_{SAM}/R_{STD}] - 1) \times 1000 \quad \text{(Formula 2)}$$

$\delta^{13}$C: $\delta^{13}$C value (‰)
$R_{SAM}$: abundance of $^{13}$C in sample gas
$R_{STD}$: abundance of $^{13}$C in standard gas When carbon dioxide derived from limestone (PDB) is used as standard gas, $R_{STD}$ is $R_{PDB} = 0.0112372$.

(I-2) $\Delta^{13}$C Value (‰)

"$\Delta^{13}$C value (‰)" means a value ($\Delta^{13}$C) obtained by subtracting the $\delta^{13}$C value before administration of a reagent (i.e., $\delta$ value of naturally occurring $^{13}$C) as a background from the $\delta^{13}$C value after administration of the reagent, as shown in the following formula.

$$\Delta^{13}C(‰) = (\delta^{13}C)_t - (\delta^{13}C)_0 \quad \text{(Formula 3)}$$

$\Delta^{13}$C(‰): amount of change in $\delta^{13}$C value (‰)
$(\delta^{13}C)_t$: $\delta^{13}$C value t hours after reagent administration (‰)
$(\delta^{13}C)_0$: $\delta^{13}$C value 0 hours before reagent administration (‰)

(I-3) $^{13}$C Concentration in Expired Air (%$^{13}$C: Atom %)

The $^{13}$C concentration in expired air (%$^{13}$C: atom %) is defined by the following formula.

$$\%^{13}C = [{}^{13}C/({}^{13}C + {}^{12}C)] \times 100$$

To convert the relative value $\delta^{13}$C defined in (I-1) into the $^{13}$C concentration (%) in the total carbon, which is a common concept of concentration, the following method can be used.

First, the numerator and denominator on the right side of the above formula are divided by $^{12}$C, and converted into R based on (Formula 1). The following formula is thus obtained.

$$\%^{13}C = [R/(R+1)] \times 100 \quad \text{(Formula 4)}$$

If $R_{SAM}$ obtained in (Formula 2) is substituted into R above and rearranged, the following formula is obtained. The $^{13}$C concentration (%$^{13}$C) can be expressed by using the $\delta^{13}$C value.

$$\%^{13}C = \{[(\delta^{13}C/1000) + 1] \times R_{PDB} \times 100\} / \{[[(\delta^{13}C/1000) + 1] \times R_{PDB}] + 1\} \quad \text{(Formula 5)}$$

%$^{13}$C: $^{13}$C concentration (atom %)
$\delta^{13}$C: $\delta^{13}$C value (‰)
$R_{PDB}$: abundance of $^{13}$C in PDB standard gas = 0.0112372

(I-4) Amount of Change in $^{13}$C Concentration ($\Delta\%^{13}$C)

As defined in the following formula, the amount of change in $^{13}$C concentration (%$^{13}$C) in expired air ($\Delta\%^{13}$C) is determined by subtracting the $^{13}$C concentration 0 hours before reagent administration [(%$^{13}$C)$_0$] from the $^{13}$C concentration t hours after reagent administration [(%$^{13}$C)$_t$].

$$\Delta\%^{13}C = (\%^{13}C)_t - (\%^{13}C)_0 \quad \text{(Formula 6)}$$

$\Delta\%^{13}$C: amount of change in $^{13}$C concentration (atom %)
$(\%^{13}C)_t$: $^{13}$C concentration t hours after reagent administration (atom %)
$(\%^{13}C)_0$: $^{13}$C concentration 0 hours before reagent administration (atom %)

(I-5) Relation Between $\Delta^{13}$C Value (‰) and Amount of Change in $^{13}$C Concentration ($\Delta\%^{13}$C)

The natural abundance (R) of $^{13}$C is about 0.011, and even when a labeled reagent is administered, the increased amount in expired air is only about +0.001 to 0.002. Thus, the natural abundance can be regarded as R→0, and Formula 4, which expresses %$^{13}$C by using R, can be approximated by the following formula.

$$\%^{13}C = [R/(R+1)] \times 100 \approx R \times 100$$

Using this approximate expression, an approximation that determines the $^{13}$C concentration (Formula 7) can be obtained as follows: first, $R_{SAM}$ is determined by Formula 2, which defines $\delta^{13}$C, substituted into R in the above formula, and rearranged.

$$\%^{13}C = [(\delta^{13}C/1000) + 1] \times R_{PDB} \times 100 \quad \text{(Formula 7)}$$

When this is substituted into Formula 6, $\Delta\%^{13}$C can be calculated from $\Delta^{13}$C, as shown in Formula 8 below.

$$\Delta\%^{13}C = (\%^{13}C)_t - (\%^{13}C)_0 \quad \text{(Formula 8)}$$
$$= \{[(\delta^{13}C)_t - (\delta^{13}C)_0]/1000\} \times R_{PDB} \times 100$$
$$= (\Delta^{13}C \times R_{PDB})/10$$

Δ%$^{13}$C: amount of change in $^{13}$C concentration (atom %)
×$^{13}$C: amount of change in δ$^{13}$C value (‰)
$R_{PDB}$: abundance of $^{13}$C in PDB standard gas=0.0112372

(II) Composition for Measuring Energy Malfunction

The composition for measuring energy malfunction of the present invention comprises, as an active ingredient, glucose labeled with at least one isotope C; the glucose is converted in the body into labeled $CO_2$ that is excreted in expired air. The labeled C-glucose used in the present invention is metabolized according to the degree of energy malfunction in the body and excreted in expired air in the form of carbon dioxide containing labeled C, which reflects the degree of energy malfunction.

There is no particular limitation on isotopes used in labeling carbon atoms of glucose in the composition, and specific examples include $^{13}$C and $^{14}$C. Such isotopes may be radioactive or non-radioactive; however, from the standpoint of safety, non-radioactive isotopes are preferable. For example, $^{13}$C is desirable for use as such an isotope.

The isotope-labeled glucose used in the composition for energy malnutrition measurement of the present invention is labeled in a manner such that at least a portion of the $CO_2$ formed through the glucose metabolic pathway in the liver is isotope-labeled. Examples of such glucose include compounds in which the carbon atom at at least one of the 1-position to the 6-position is isotope-labeled. Specific examples include 1-$^{13}$C-labeled glucose, 2-$^{13}$C-labeled glucose, and 3-$^{13}$C-labeled glucose. Specific examples of isotope-labeled glucose include glucose in which the carbon atom of the 1-position and/or 6-position is isotope-labeled, glucose in which the carbon atom of the 2-position and/or 5-position is isotope-labeled, glucose in which the carbon atom of the 3-position and/or 4-position is isotope-labeled, and glucose in which all of the carbon atoms at the 1-, 2-, 3-, 4-, 5-, and 6-positions are isotope-labeled. Preferable examples of isotope-labeled glucose include glucose in which the carbon atom at the 3-position and/or 4-position is isotope-labeled (e.g., 3-$^{13}$C-labeled glucose and/or 4-$^{13}$C-labeled glucose) and glucose in which all of the carbon atoms at the 1-, 2-, 3-, 4-, 5-, and 6-positions are isotope-labeled. These glucoses may be used solely, or in a combination of two or more kinds.

There is no particular limitation on the method for labeling glucose with isotopes such as $^{13}$C or $^{14}$C, and a wide variety of commonly used methods may be employed (Yasuto Sasaki, "5.1 *Antei Doitai no Rinsho Shindan heno Oyo* [5.1 Application of Stable Isotopes in Clinical Diagnosis]," *Kagaku no Ryoiki* [Journal of Japanese Chemistry] 107, pp. 149-163 (1975), Nankodo; Kajiwara, RADIOISOTOPES, 41, 45-48 (1992); etc.). Such isotope-labeled compounds, particularly the $^{13}$C-labeled-glucose used in the Examples described later, are commercially available as conveniently usable commercial products.

There is no particular limitation on the composition of the present invention in terms of its form, components other than the labeled C-glucose, proportion of each component, preparation method of the composition, etc., as long as the labeled C-glucose is absorbed in the body, and excreted in expired air in the form of labeled carbon dioxide after metabolism. The composition of the present invention may consist only of labeled C-glucose.

There is no particular limitation on the form of the composition of the present invention, as long as the effects of the present invention are ensured. For example, the form of the composition may be an oral dosage form or a parenteral dosage form. Examples of oral dosage forms include any oral dosage forms, such as solutions (including syrup), suspensions, emulsions, and like liquids; tablets (with and without coating), chewable tablets, capsules, pills, pulvis (powders), fine particles, granules, and like solids. Examples of parenteral dosage forms include any parenteral dosage forms, such as injections and drops (in liquid, suspension, or emulsion form). The form of the composition is preferably an oral dosage form, which is a non-invasive measurement method. On the other hand, from the standpoint of performing further rapid and highly accurate measurement, an injection dosage form, in particular, an intravenous dosage form, is preferable.

For example, when the composition of the present invention is formed into a liquid form such as a liquid, a suspension, an emulsion, or like injection dosage form, the composition of the present invention may consist only of the labeled C-glucose, which is an active ingredient, i.e., may substantially be formed into a liquid form by combining labeled C-glucose with an arbitrary solvent such as physiological saline solution, distilled water for injection, purified water, or the like. However, the present invention is not limited to this example. Further, as long as the effects of the present invention are not adversely affected, any pharmaceutically acceptable carriers and/or additives that are generally used in this field may be added as other components, as necessary. Examples of carriers and/or additives include carriers and/or additives commonly used, such as tonicity-adjusting agents (e.g., sodium chloride etc.), pH adjusters (e.g., hydrochloric acid, sodium hydroxide, etc.), buffers (e.g., boric acid, sodium monohydrogen phosphate, sodium dihydrogen phosphate, etc.), preservatives (e.g., benzalkonium chloride etc.), and thickeners (e.g., carboxyvinyl polymers etc.).

In this case, insofar as the composition of the present invention can be made into a liquid form when used, the composition may have a solid form, such as a freeze-dried preparation or a spray-dried preparation, that is to be dissolved in a physiological saline solution, distilled water for injection, purified water, or the like when used.

When the composition of the present invention is formed into, for example, tablets, chewable tablets, capsules, pills, pulvis (powders), fine particles, granules, and like solid forms, various carriers and/or additives suitable for such forms may be used. Tablets may be provided with an ordinary coating, if necessary. Examples thereof include sugar-coated tablets, gelatin-coated tablets, film-coated tablets, double-coated tablets, multi-coated tablets, etc. Capsules are prepared in a commonly employed method, i.e., mixing the isotope-labeled glucose, which is an active ingredient, with various components mentioned above, if necessary, and placing it in a hard gelatin capsule, a soft capsule, etc.

When arbitrary components, such as carriers or additives, are used in the composition of the present invention, the amount of the labeled C-glucose as an active ingredient is not particularly limited; however, for example, the amount of the labeled C-glucose is 1 to 99 wt % in the composition. The amount may be appropriately adjusted within this range.

The arbitrary components, such as carriers or additives, are not limited insofar as the effects of the present invention are ensured. Examples of carriers or additives include lactose, sucrose, dextrin, mannitol, xylitol, sorbitol, erythritol, calcium dihydrogen phosphate, sodium chloride, glucose, urea, starch, calcium carbonate, kaolin, crystalline cellulose, silicic acid, water, ethanol, simple syrup, glucose liquid, starch liquid, gelatin liquid, carboxymethyl cellulose, sodium carboxymethyl cellulose, shellac, methyl cellulose, hydroxypropylmethyl cellulose, hydroxypropyl cellulose, potassium phosphate, polyvinyl alcohol, polyvinyl pyrrolidone, pullulan, dry starch, sodium alginate, agar powder, laminaran powder, sodium bicarbonate, polyoxyethylene sorbitan fatty acid esters, sodium lauryl sulfate, monoglyceride stearate, carmellose calcium, low substituted hydroxypropyl cellulose, carmellose, croscarmellose sodium, sodium carboxymethyl starch, crospovidone, stearic acid, cacao butter, hydrogenated oil, polysorbate 80, quaternary-ammonium base, sodium lauryl sulfate, glycerin, bentonite, colloidal silicic acid, purified talc, stearate, boric acid powder, polyethylene glycol, colloidal silicic acid, sucrose fatty acids, hardened oil, citric acid, anhydrous citric acid, sodium citrate, sodium citrate dihydrate, anhydrous sodium monohydrogenphosphate, anhydrous sodium dihydrogenphosphate, sodium hydrogen phosphate, iron oxide, β-carotene, titanium oxide, food colors, copper chlorophyll, riboflavin, ascorbic acid, and various sweeteners.

The forms and arbitrary components may be appropriately selected according to need by a person skilled in the art.

The composition of the present invention is not limited to such a pharmaceutical preparation, as long as the composition contains the labeled C-glucose and the effects of the present invention are not adversely affected. The labeled C-glucose may be combined with any foodstuff and formed into solid food, fluid food, or liquid food.

The composition of the present invention is used as a composition (administrative reagent) to be applied to a liver disease test subject in the methods described later. More specifically, the composition of the present invention may be used as a reagent for the measurement of energy malnutrition in a liver disease test subject described later. Further, the composition of the present invention may also be used as a reagent for the determination as to whether a liver disease test subject is in an energy malnutrition state described later. Further, the composition of the present invention may also be used as a reagent for the determination of necessity of nutrition therapy for a liver disease test subject having energy malnutrition described later. These methods may be performed based on abundance of carbon dioxide (abundance of substance) in expired air (the ratio of labeled $CO_2$ amount to unlabeled $CO_2$ amount, or the ratio of labeled $CO_2$ amount to total $CO_2$ amount) obtained from a liver disease test subject. The details of the methods are shown below.

The target subject of the composition of the present invention is also not limited insofar as the effects of the present invention are not impaired. Examples of the target subjects include test subjects with liver diseases (liver disease test subject). More preferably, the target subjects are test subjects with liver cirrhosis (liver cirrhosis test subject), further preferably test subjects with liver cirrhosis accompanied by energy malnutrition. Examples of liver disease test subjects include test subjects having a pre-liver cirrhosis condition, such as non-alcoholic fatty liver disease (NAFLD), non-alcoholic steatohepatitis (NASH), viral hepatitis (hepatitis B, hepatitis C, etc.), alcoholic liver disease, primary biliary cirrhosis, primary sclerosing cholangitis, hemochromatosis, or autoimmune hepatitis, and liver cirrhosis test subjects. Further, the liver disease test subject of the present invention may be a liver disease test subject having a disease such as diabetes, borderline diabetes, insulin resistance, and the like that may be worsened in symptom by a diet therapy; or may be a liver disease test subject who does not have such a disease. The target subject may be suitably selected or determined according to need from the standpoint of the method and the diet therapy described later.

The test subjects (target subjects) of the present invention are humans, or mammals other than humans. Examples of mammals other than humans include mice, rats, guinea pigs, rabbits, dogs, cats, monkeys, pigs, cattle, horses, and the like. Mice, rats, guinea pigs, rabbits, dogs, and monkeys are preferable.

The amount of the labeled C-glucose (active ingredient) in the composition of the present invention may be suitably set or adjusted for each case (for example, depending on the type of the test subject, the condition of the liver disease test subject, whether it is in a fasting period or non-fasting period), the form of the composition, and the like. When the form of the composition of the present invention is an oral dosage form or an intravenous dosage form, the amount of a single dose (administration amount) may be adjusted so that the amount of the labeled C-glucose (active ingredient) is in the range of 5 mg/body to 50 g/body, and preferably 10 mg/body to 25 g/body.

The present invention enables easy, rapid and highly accurate measurement of energy malnutrition, and also enables the later-described method to be performed more easily, rapidly, and with high accuracy.

(III) Method for Measuring Energy Malnutrition in Liver Disease Test Subject

The present invention provides a method for measuring energy malnutrition in a liver disease test subject, comprising steps (1-a) and (1-b) below. Specifically, the present invention provides a method for measuring energy malnutrition, comprising step (1-a) of collecting expired air containing labeled carbon dioxide that is generated in the body of a liver disease test subject by being converted from a composition containing, as an active ingredient, glucose labeled with at least one isotope C; and step (1-b) of determining the ratio of labeled $CO_2$ amount to unlabeled $CO_2$ amount, or the ratio of labeled $CO_2$ amount to total $CO_2$ amount in expired air.

The "composition containing, as an active ingredient, glucose labeled with at least one isotope C" used in the present invention is similar to the composition of the present invention for energy malnutrition measurement described above. Accordingly, step (1-a) of the method may also be expressed as "a step of collecting expired air containing labeled carbon dioxide generated by conversion of the composition of the present invention for energy malnutrition measurement in the body of a liver disease test subject." Accordingly, the form of the "composition containing, as an active ingredient, glucose labeled with at least one isotope C," the content of the labeled C-glucose, the dose, components such as arbitrary carriers or additives, target subjects, and the like are similar to those of the composition for energy malnutrition measurement described above. Further, accordingly, the composition of the present invention for energy malnutrition measurement described above may also be expressed as a composition for the measurement of energy malnutrition in a liver disease test subject.

In the present invention, as described above, the labeled C-glucose is metabolized in the body of a liver disease test subject according to the degree of energy malnutrition, and excreted in expired air in the form of carbon dioxide containing labeled C, which reflects the degree of energy malnutrition, i.e., the degree of the metabolism in the liver. The excreted expired air may be collected by a person skilled in the art according to the method of a previously known breath test.

Further, in the present invention, the test subject may be in a fasting state or non-fasting state immediately before the method is performed, and is preferably in a fasting state.

Particularly for humans, the test subject is preferably in a fasting state. When the liver disease test subject is fasted immediately before the method is performed, in performing step (1-a), the liver disease test subject is fasted, for example, at least 2 hours, preferably at least 4 hours before the administration of the composition. However, the present invention is not limited to this example. Intake of water is acceptable. When the liver disease test subject is in a non-fasting state immediately before the method is performed, the liver disease test subject has a normal diet, as usual.

In the present invention, abundance of carbon dioxide (the ratio of labeled $CO_2$ amount to unlabeled $CO_2$ amount, or the ratio of labeled $CO_2$ amount to total $CO_2$ amount) in expired air obtained in step (1-a) is determined in step (1-b). The abundance of carbon dioxide in expired air may be determined, for example, as follows according to a previously known method. However, the present invention is not limited to this method. In the example below, the ratio of $^{13}CO_2$ amount to total $CO_2$ amount is determined using a composition containing $^{13}C$-labeled glucose as an active ingredient (that is, the labeled $CO_2$ to be measured is $^{13}CO_2$). A method using other labeled C-glucoses, such as $^{14}C$-labeled glucose, may be performed in a similar manner.

The abundance of carbon dioxide contained in the collected expired air (the ratio of $^{13}CO_2$ amount to total $CO_2$ amount) is calculated according to the below-described method as the amount of change in $^{13}C$ concentration ($\Delta\%^{13}C$).

More specifically, the $^{13}C$ concentration in total carbon contained in expired air collected t hours after administration of the composition to a test subject ($^{13}C$ concentration in expired air, $^{13}C$ concentration atom %, $(\%^{13}C)_t$) is determined. Additionally, the $^{13}C$ concentration in total carbon contained in expired air collected in advance before administration, preferably 0 hours before administration, ($^{13}C$ concentration in expired air, $^{13}C$ concentration atom %, $(\%^{13}C)_0$) is determined. Further, $(\%^{13}C)_0$ is subtracted from $(\%^{13}C)_t$ according to Formula 6, thereby obtaining the amount of change in the $^{13}C$ concentration ($\Delta\%^{13}C$ (atom %)).

$$C \text{ concentration(atom \%)} = [^{13}C/(^{13}C+^{13}C)] \times 100$$

$$\Delta\%^{13}C = (\%^{13}C)_t - (\%^{13}C)_0 \quad \text{(Formula 6)}$$

$\Delta\%^{13}C$: amount of change in $^{13}C$ concentration (atom %)
$(\%^{13}C)_t$: $^{13}C$ concentration t hours after reagent administration (atom %)
$(\%^{13}C)_0$: $^{13}C$ concentration 0 hours before reagent administration (atom %)

If necessary, the amount of change in the $^{13}C$ concentration ($\Delta\%^{13}C$) may be converted into $\Delta^{13}C$ value (‰) (amount of change in $\delta^{13}C$ value (‰) or DOB (‰)) based on Formula 5 and Formula 3.

$$\%^{13}C = \{[(\delta^{13}C/1000)+1] \times R_{PDB} \times 100\}/\{[[(\delta^{13}C/1000)+1] \times R_{PDB}]+1\} \quad \text{(Formula 56)}$$

$\%^{13}C$: $^{13}C$ concentration (atom %)
$\delta^{13}C$: $^{13}C$ value (‰)
$R_{PDB}$: abundance of $^{13}C$ in PDB standard gas=0.0112372

$$\Delta^{13}C(‰) = (\delta^{13}C)_t - (\delta^{13}C)_0 \quad \text{(Formula 3)}$$

$\Delta^{13}C$(‰): amount of change in $\delta^{13}C$ value (‰)
$(\delta^{13}C)_t$: $\delta^{13}C$ value t hours after reagent administration (‰)
$(\delta^{13}C)_0$: $\delta^{13}C$ value 0 hours before reagent administration (‰)

As is clear from the above, the method of the present invention enables easy and rapid determination of the ratio of $^{13}CO_2$ amount to total $CO_2$ amount in expired air with high accuracy. Further, in addition to this ratio, the method of the present invention also enables easy, rapid, and highly accurate determination of, for example, the ratio of labeled $CO_2$ amount to unlabeled $CO_2$ amount in a manner similar to that of a previously known method.

The measurement and the analysis of the labeled $CO_2$, the unlabeled $CO_2$, and the total $CO_2$ contained in an expired air sample may be performed based on a previously known method; such measurement and analysis are known to a person skilled in the art. For example, various methods are used for the measurement and analysis of the labeled $CO_2$ depending on whether the isotope used is radioactive or non-radioactive. However, the measurement and analysis may be performed by a commonly used analysis method, such as the liquid scintillation counter method, mass spectrometry, infrared spectroscopy, emission spectrometry, or the magnetic resonance spectrum method. From the viewpoint of measurement accuracy, infrared spectroscopy and mass spectrometry are preferable.

The phrase "t hours after the administration of the composition to a liver disease test subject" means time points t hours after the composition, i.e., labeled C-glucose, is administered to a liver disease test subject. Accordingly, time "t" may also be referred to as expired air collection time t. The expired air collection time t is not limited insofar as the effects of the present invention are ensured. However, the expired air collection time t is, for example, any time between 1 to 120 minutes after the administration of the labeled C-glucose to a test subject, and a person skilled in the art may set a suitable time according to the above range.

For example, for humans, the expired air collection time t (unit: minutes) is preferably any time between 1 to 120 minutes, more preferably between 1 to 90 minutes after the administration of the labeled C-glucose. For non-human subjects, a person skilled in the art may set a suitable time by referring to the above range.

Further, although it is not limited insofar as the effects of the present invention are ensured, the ratio of labeled $CO_2$ amount to unlabeled $CO_2$ amount, or the ratio of labeled $CO_2$ amount to total $CO_2$ amount in expired air may be determined by calculating an area under the curve ($AUC_t$) in a graph showing changes over time of $\Delta$-labeled C(‰) or labeled C excretion speed (% dose/hr), for example, in a graph in which the ordinate axis denotes $\Delta$-labeled C(‰) or labeled C excretion speed (% dose/hr) and the abscissa axis denotes a time elapsed after the administration of labeled C-glucose (expired air collection time: t) (minutes). More specifically, for example, when the $^{13}C$-labeled glucose is used, the ratio may be determined by calculating an area under the curve ($AUC_t$) in a graph showing changes over time of $\Delta^{13}C$(‰) or $^{13}C$ excretion speed (% dose/hr), for example, in a graph in which the ordinate axis denotes $\Delta^{13}C$(‰) or $^{13}C$ excretion speed (% dose/hr) and the abscissa axis denotes a time elapsed after the administration of $^{13}C$-glucose (expired air collection time: t) (minutes). In this case, when the ordinate axis denotes $\Delta^{13}C$(‰) or $^{13}C$ excretion speed (% dose/hr), the calculation result of an area under the curve between the administration of $^{13}C$-glucose to a liver disease test subject and expired air collection time t may be expressed as [area under $\Delta^{13}C$(‰) or $^{13}C$ excretion speed (% dose/hr)-0 minutes after $^{13}C$-glucose administration to expired air collection time t curve]($AUC_{t-0}$). Further, when the ordinate axis denotes $\Delta^{13}C$(‰) or $^{13}C$ excretion speed (% dose/hr), the calculation result of an area under the curve between expired air collection time $t_1$ minute to expired air collection time $t_2$ minutes may be expressed as

[area under $\Delta^{13}C(‰)$ or $^{13}C$ excretion speed (% dose/hr)-expired air collection time $t_1$ minute to expired air collection time $t_2$ curve] ($AUC_{t2-t1}$). The calculation of area under the curve may be performed according to a previously known calculation method, and a person skilled in the art would easily understand the method. Further, the calculation of $^{13}C$ excretion speed (% dose/hr) may also be performed according to a previously known calculation method, and a person skilled in the art would easily understand the method. Further, in the method of the present invention, the ordinate axis is not limited to the axes shown above; insofar as the effects of the present invention are ensured, a person skilled in the art may suitably determine the ordinate axis.

When an area under the curve is used, as in the case above, expired air collection time t is also selected from, for example, the range between 1 to 120 minutes after the administration of the labeled C-glucose. For example, for humans, expired air collection time t is preferably any time between 1 to 120 minutes, more preferably between 1 to 90 minutes after the administration of the labeled C-glucose, a person skilled in the art may set a suitable time according to the above range. Further, for non-humans, a person skilled in the art may set a suitable time according to the above range.

Accordingly, the present invention may also be regarded as providing a step of determining the ratio of labeled $CO_2$ amount to unlabeled $CO_2$ amount, or the ratio of labeled $CO_2$ amount to total $CO_2$ amount in collected expired air (wherein the expired air is expired air that is excreted from the body and contains labeled carbon dioxide generated by conversion of the composition containing, as an active ingredient, glucose labeled with at least one isotope C in the body of a liver disease test subject). This step is referred to as step (1-ab).

According to the method of the present invention, by performing such steps, the ratio of labeled $CO_2$ amount to unlabeled $CO_2$ amount, or the ratio of labeled $CO_2$ amount to total $CO_2$ amount in expired air may be easily and rapidly determined with high accuracy.

Further, the method for measuring energy malnutrition of the present invention may further comprise step (1-c) below. More specifically, the present invention may further comprise a step of comparing "the ratio of labeled $CO_2$ amount to unlabeled $CO_2$ amount, or the ratio of labeled $CO_2$ amount to total $CO_2$ amount in expired air" obtained in step (1-b) or step (1-ab) (subject value) with "the ratio of labeled $CO_2$ amount to unlabeled $CO_2$ amount, or the ratio of labeled $CO_2$ amount to total $CO_2$ amount in expired air" in healthy subject (control value), thereby determining whether the subject value is lower than the control value. In step (1-c), the subject value and the control value thus obtained are compared, thereby determining that the subject value is "lower" when the subject value is lower than the control value, and determining that the subject value is "higher or equivalent" when the subject value is higher than or equivalent to the control value.

The determination of a control value of healthy subject may be performed by using time t, which is the same as expired air collection time t used for the calculation of the subject value, in a similar calculation manner. Examples of the control value include a value calculated by the above method, and a value equivalent to the calculated value. Further, examples of healthy subjects include, as in the test subjects, humans, or mammals other than humans. A healthy subject means a subject who is at least not in an energy malnutrition state. Further, since an energy malnutrition state is a symptom observed particularly in liver cirrhosis, in the present invention, for example, a healthy subject is preferably a subject who is not in an energy malnutrition state and is healthy with regard to liver cirrhosis. More preferably, a healthy subject is a subject who is healthy with regard to liver cirrhosis, i.e., a subject in which liver cirrhosis has not developed, and who is also not in a stage before onset of liver cirrhosis (non-liver cirrhosis subject). Further, particularly preferable examples of healthy subjects include a healthy subject without a disease having adverse effects on the measurement of energy malnutrition, i.e., the calculation of the ratio and the judgment, and who is also not in a stage before onset of such diseases.

Such a method of the present invention enables easy, rapid, and highly accurate determination of the ratio of labeled $CO_2$ amount to unlabeled $CO_2$ amount, or the ratio of labeled $CO_2$ amount to total $CO_2$ amount in expired air, thereby easily and rapidly determining whether the subject value is lower than the control value with high accuracy. Further, such a method of the present invention enables comprehension of the degree of the difference (higher or lower) of the subject value relative to the control value; and also enables, based on the degree of the difference, comprehension of the degree of the energy malnutrition state.

Further, although it is not limited insofar as the effects of the present invention are ensured, in terms of further alleviating, for example, physical or mental pain of liver disease test subjects, in the method of the present invention, step (1-a) is performed, for example, for humans, within 120 minutes, more preferably within 1 to 90 minutes after the administration of labeled C-glucose to a liver disease test subject. Further, in terms of further rapidly measuring energy malnutrition, in the method of the present invention, steps (1-a) and (1-b), or step (1-ab) is performed within 120 minutes, more preferably within 1 to 90 minutes after the administration of labeled C-glucose to a liver disease test subject. Further, in terms of furthermore rapidly measuring energy malnutrition, in the method of the present invention, steps (1-a), (1-b) and (1-c), or (1-ab) and (1-c) are performed within 120 minutes, more preferably within 1 to 90 minutes after the administration of labeled C-glucose to a liver disease test subject. However, the present invention is not limited to these examples. The time (required time) is the total time required for the individual steps, i.e., the steps from the administration of labeled C-glucose to a liver disease test subject to the end of the above steps; the steps may be performed either continuously, or non-continuously. For non-humans, a person skilled in the art may set a suitable time by referring to the above range.

Such a present invention enables measurement of energy malnutrition in a liver disease test subject easily and rapidly with high accuracy based on the calculation values or the judgments. Further, the present invention enables evaluation of energy malnutrition state of a liver disease test subject using the calculation values or the judgments as indices. Further, when it is determined that the subject value is lower than the control value in step (1-c), it is determined that the test subject is in an energy malnutrition state; and when the subject value is higher than or equivalent to the control value, it is determined that the test subject is not in an energy malnutrition state. As is thus clear, the present invention further enables easy, rapid, and highly accurate determination as to whether a liver disease test subject is in an energy malnutrition state.

As explained above, the present invention enables easy, rapid, and highly accurate measurement and evaluation of energy malnutrition merely by performing a breath test using isotope-labeled C-glucose. Accordingly, the present invention alleviates or resolves the drawbacks of previously known methods using indirect calorimetry, i.e., the drawbacks such that indirect calorimetry is expensive, requires a special device, can only be performed in limited institutions, can only thus be applied to a limited number of patients, requires complicated operation, requires the patients to be kept quiet in bed and prevented from falling asleep, requires monitoring by an observer, and is an indirect and unclear evaluation.

Further, since the method of the present invention can thus be performed easily, rapidly, and with high accuracy, the measurement or evaluation of other diseases such as diabetes, borderline diabetes, or insulin resistance can also be immediately performed. Therefore, the present invention enables comprehension of the presence or absence of other diseases and measurement of energy malnutrition more easily and rapidly than previously known methods. Further, even when a liver disease test subjects has other diseases such as diabetes, the method of the present invention enables easy, rapid, and highly accurate measurement of energy malnutrition. Further, accordingly, the present invention enables appropriate and rapid diet therapy for energy malnutrition, and thereby contributes to improvement in prognosis or quality of life with regard to energy malnutrition. Further, the present invention can be easily used for monitoring of the therapeutic effects or the degree of progression with regard to energy malnutrition state.

(IV) Method for Determining Whether a Liver Disease Test Subject is in an Energy Malnutrition State As described above, the present invention enables determination as to whether a liver disease test subject is in an energy malnutrition state based on the calculation values or the judgments obtained or made in the method for measuring energy malnutrition. Accordingly, the present invention further provides a method for determining whether a liver disease test subject is in an energy malnutrition state.

More specifically, the present invention provides a method for determining whether a liver disease test subject is in an energy malnutrition state, comprising steps (2-a) and (2-b) below. Specifically, the present invention provides a method for determining whether a liver disease test subject is in an energy malnutrition state, comprising step (2-a) of administering, to a liver disease test subject, a composition containing, as an active ingredient, glucose labeled with at least one isotope C, which is converted into labeled carbon dioxide in the body and excreted in expired air, and collecting expired air; and step (2-b) of determining the ratio of labeled $CO_2$ amount to unlabeled $CO_2$ amount, or the ratio of labeled $CO_2$ amount to total $CO_2$ amount in expired air.

Regarding steps (2-a) and (2-b), the liver disease test subject, collection of expired air, the ratio of labeled $CO_2$ amount to unlabeled $CO_2$ amount, or the ratio of labeled $CO_2$ amount to total $CO_2$ amount in expired air, the composition, the formulation thereof, labeled C-glucose, components such as arbitrary carriers or additives, the contents of the components, dose, administration method, explanations of target subjects, executions of the steps, and the like are similar to those of steps (1-a) and (1-b), and a person skilled in the art would easily understand steps (2-a) and (2-b) based on the explanations above. Further, accordingly, the composition for energy malnutrition measurement described above may also be referred to as a composition for determining whether a liver disease test subject is in an energy malnutrition state.

Further, as in the above explanation, in the present invention, the test subject may be in a fasting state or non-fasting state immediately before the test is performed, and is preferably in a fasting state. The above explanation is applied both for a test in a fasting state, and a test in a non-fasting state.

Further, the present invention provides a method for determining whether a test subject is in an energy malnutrition state, further comprising step (2-c) below. More specifically, the present invention provides a method for determining whether a test subject is in an energy malnutrition state, comprising step (2-c) of comparing "the ratio of labeled $CO_2$ amount to unlabeled $CO_2$ amount, or the ratio of labeled $CO_2$ amount to total $CO_2$ amount in expired air" in the test subject obtained in step (2-b) (subject value) with "the ratio of labeled $CO_2$ amount to unlabeled $CO_2$ amount, or the ratio of labeled $CO_2$ amount to total $CO_2$ amount in expired air" in healthy subject (control value), and determining that the test subject is in an energy malnutrition state when the subject value is lower than the control value, and determining that the test subject is not in an energy malnutrition state when the subject value is equivalent to or higher than the control value.

Also in step (2-c), the subject value, control value, healthy subject, and procedures of the comparison between the values are similar to those of step (1-c) above, and a person skilled in the art would easily understand and carry out step (2-c) based on the explanations above. Further, by comparing the subject value and the control value in step (2-c), it is determined that the test subject is in an energy malnutrition state when the subject value is lower than the control value, and that the test subject is not in an energy malnutrition state when the subject value is equivalent to or higher than the control value.

As described above, the present invention enables easy, rapid, and highly accurate determination as to whether a test subject is in an energy malnutrition state. Further, such a present invention enables comprehension of the degree of the difference (higher or lower) of the subject value relative to the control value; and also enables, based on the degree of the difference, comprehension of the degree of the energy malnutrition state.

Examples of typical treatments of energy malnutrition include a diet therapy, in particular, a method of administering a branched-chain amino acid (BCAA) preparation, and late-evening snacking (LES) in which the patients have a small amount of meal before bedtime so as to avoid energy shortage in the liver at night. The details of these diet therapies are publicly known, and a person skilled in the art may set suitable conditions. On the other hand, such a diet therapy, in particular, the late-evening snacking, increases the frequency of meals; further, since such a therapy LES allows the patient to have a meal before bedtime, there is a risk of obesity due to extra calories. Further, for patients with a disease such as diabetes, borderline diabetes, insulin resistance, or the like, that may be worsened in symptom by a diet therapy, it is necessary to consider execution of a diet therapy, in particular, late-evening snacking or similar treatments, in consideration of the presence of these diseases.

Accordingly, in performing a diet therapy, which is a typical treatment of energy malnutrition, it is preferable to know whether the liver disease test subject diagnosed with an energy malnutrition state has a disease that may be worsened in symptom by a diet therapy, such as diabetes, borderline diabetes, or insulin resistance.

For example, in terms of avoiding the risk of worsening the symptom by a diet therapy, the liver disease test subject diagnosed with an energy malnutrition state preferably does not have a disease that may be worsened by a diet therapy, such as diabetes, borderline diabetes, or insulin resistance.

To this end, the present invention may further comprise step (2-d) of excluding one or more test subjects having a disease that may be worsened in symptom by a diet therapy for energy malnutrition (for example, at least one disease selected from the group consisting of diabetes, borderline diabetes and insulin resistance) from the liver disease test subjects before step (2-a), or excluding one or more test subjects having a disease that may be worsened in symptom by a diet therapy for energy malnutrition (for example, at least one disease selected from the group consisting of diabetes, borderline diabetes and insulin resistance) from liver disease test subjects determined to have a subject value lower than the control value, and thus have an energy malnutritional state in step (2-c).

Further, the present invention may further comprise step (2-e) of determining whether the liver disease test subject is a test subject having a disease that may be worsened in symptom by a diet therapy for energy malnutrition (for example, at least one disease selected from the group consisting of diabetes, borderline diabetes and insulin resistance) before the exclusion in step (2-d).

The determination as to whether the test subject has a disease that may be worsened in symptom by a diet therapy may be performed by any previously known or common diagnosis methods, or based on the standards of such methods. A person skilled in the art would easily understand these methods.

Examples of diagnoses of diabetes, borderline diabetes, and insulin resistance include diagnoses based on blood glucose level, glucose tolerance test, HbA1c (hemoglobin A1c), HOMA-R (homeostasis model assessment ratio) and the like. For example, according to a previously known diagnosis method, the patient is diagnosed with diabetes, for example, when the blood glucose level on an empty stomach is 126 mg/dl or more, when the blood glucose level two hours after glucose was loaded is 200 mg/dl or more in a 75 g oral glucose tolerance test, or when HbA1c is 6.5% or more. However, the present invention is not limited to these ranges. Further, the patient is diagnosed with borderline diabetes, for example, when the blood glucose level on an empty stomach is 110 mg/dl to less than 126 mg/dl, or when the blood glucose level two hours after glucose was loaded is 140 mg/dl to less than 200 mg/dl in a 75 g oral glucose tolerance test. Further, the patient is determined to be non-diabetic, for example, when the blood glucose level on an empty stomach is less than 110 mg/dl, or when the blood glucose level two hours after glucose was loaded is less than 140 mg/dl in a 75 g oral glucose tolerance test. Further, for example, according to a previously known diagnosis method, when HOMA-R, which is calculated from the insulin level on an empty stomach and the blood Glucose level on an empty stomach, is 1.6 or less, the patient is determined to be free of insulin resistance; and when HOMA-R is higher than 1.75, or further higher than 2.5, the patient is determined to have insulin resistance. The determination may also be made in combination with blood glucose level on an empty stomach.

As described above, the method of the present invention may be suitably applied to a liver disease test subject who does not have a disease, such as diabetes, borderline diabetes, or insulin resistance, that may be worsened in symptom by a diet therapy.

Further, the method of the present invention may also be suitably applied to a liver disease test subject having a disease, such as diabetes, that may be worsened in symptom by a diet therapy. An example is more specifically explained below. In the method of the present invention, a test subject having a liver disease, in particular, liver cirrhosis, and diabetes at the same time may have a subject value further lower than the control value, than a test subject having only a liver disease. Accordingly, the method of the present invention may also be suitably applied to a test subject who has liver disease and diabetes at the same time. When the test subject has a subject value further lower than the control value, it is possible to easily and rapidly, and with high accuracy, determine whether a diet therapy for energy malnutrition should be preferentially performed despite the diabetic condition of the test subject. The determination as to whether the liver disease test subject has a disease, such as diabetes, that may be worsened in symptom by a diet therapy, may be performed by further performing a step of, as in step (2-e), determining whether the liver disease test subject has a disease that may be worsened in symptom by a diet therapy for energy malnutrition.

As is clear from above, the present invention alleviates or resolves the drawbacks of previously known methods for determining energy malnutrition using indirect calorimetry, i.e., for example, the drawbacks such that indirect calorimetry is expensive, requires a special device, can only be performed in limited institutions, can only thus be applied to a limited number of patients, requires complicated operation, requires the patients to be kept quiet in bed and prevented from falling asleep, requires monitoring by an observer, and has an indirect and unclear evaluation. Further, it is possible to easily and rapidly determine whether a liver disease test subject is in an energy malnutrition state with high accuracy. Therefore, the execution of the present invention also enables immediate measurement and evaluation with respect to other diseases such as diabetes, borderline diabetes, insulin resistance, and the like. In particular, as described above, the present invention can be a replacement for the previously known respiratory quotient, and enables determination of the presence or absence, the degree, and the appropriate diet therapy with regard to energy malnutrition, while excluding diabetes, borderline diabetes, insulin resistance, and the like, or while considering the presence of these diseases during a series of diagnoses.

In terms of further reducing constraint, and physical or mental pain of the liver disease test subject, in the present invention, for example, step (2-a) is preferably performed, for humans, within 120 minutes, more preferably within 1 to 90 minutes after the administration of labeled C-glucose to a liver disease test subject. However, the present invention is not limited to this range. Further, more preferably, in terms of further rapidly determining whether a liver disease test subject is in an energy malnutrition state, in the present invention, steps (2-a) and (2-b) are preferably performed within 120 minutes, further preferably within 1 to 90 minutes after the administration of labeled C-glucose to a liver disease test subject. Particularly preferably, steps (2-a), (2-b), and (2-c) are performed within 120 minutes, further preferably within 1 to 90 minutes after the administration of labeled C-glucose to a liver disease test subject. However, the present invention is not limited to this range. Further, in the present invention, when step (2-d) is performed in addition to these steps, all of the steps are preferably performed, for example, within 120 minutes, more preferably within 1 to 90 minutes. Further, in the present invention, when step (2-e) is performed in addition to these steps, all of the steps are preferably performed, for example, within 120 minutes, more preferably within 1 to 90 minutes. The time (required time) is the total time required for individual steps, i.e., the steps from the administration of labeled C-glucose to a liver disease test subject to the end of the above steps; the steps may be performed either continuously or non-continuously. For non-humans, a person skilled in the art may set a suitable time by referring to the above range.

Such a method of the present invention enables easy, rapid, and highly accurate determination as to whether a liver disease test subject is in an energy malnutrition state. Therefore, the present invention alleviates or resolves the drawbacks of previously known methods for evaluating an energy malnutrition state using a means such as indirect calorimetry, i.e., for example, the drawbacks such that it is expensive, requires a special device and thus can only be performed in limited institutions, requires complicated operation, has an indirect and unclear evaluation, causes the patients and observers mental or physical pain, and can only be applied in a limited number of patients. Accordingly, the present invention is useful as a replacement for the previously known respiratory quotient.

Further, as described above, when a liver disease test subject is determined to have an energy malnutrition state, it is also determined that the test subject needs a nutrition therapy based on such a determination. Further, based on this determination, consideration or execution of an appropriate treatment of the energy malnutrition state becomes possible. Further, when a liver disease test subject is determined to be free of an energy malnutrition state, for example, based on this determination, it is determined that the test subject does not need nutrition therapy for energy malnutrition. Further, the present invention can be easily used for monitoring of the therapeutic effects or the degree of progression with regard to energy malnutrition state.

Further, as is clear from the above, since the present invention greatly alleviates the drawbacks of previously known methods for measuring respiratory quotient using indirect calorimetry, it can be immediately applied to measurement and evaluation with regard to other diseases such as diabetes, borderline diabetes, insulin resistance, and the like. Therefore, the present invention enables comprehension of an energy malnutrition state, and comprehension of the presence or absence of other diseases more easily and rapidly than the previously known methods. Further, the method of the present invention enables easy, rapid, and highly accurate determination as to whether a liver disease test subject has energy malnutrition, even when the test subject has other diseases such as diabetes. As is thus clear, the present invention enables more appropriate and rapid diet therapy for energy malnutrition, and thereby contributes to improvement in prognosis or quality of life with regard to energy malnutrition.

(V) Method for Determining the Necessity of Nutrition Therapy for Liver Disease Test Subject Having Energy Malnutrition As explained above, the present invention enables determination of the necessity of nutrition therapy for a liver disease test subject having energy malnutrition based on the calculation values or the judgments described above. Accordingly, the present invention provides a method for determining the necessity of a nutrition therapy for a liver disease test subject having energy malnutrition, comprising steps (3-a) to (3-c) below.

More specifically, the present invention provides a method for determining the necessity of nutrition therapy for energy malnutrition, comprising step (3-a) of collecting expired air containing labeled carbon dioxide that is generated in the body of a liver disease test subject by being converted from a composition containing, as an active ingredient, Glucose labeled with at least one isotope C; step (3-b) of determining the ratio of labeled $CO_2$ amount to unlabeled $CO_2$ amount, or the ratio of labeled $CO_2$ amount to total $CO_2$ amount in expired air; and step (3-c) of comparing "the ratio of labeled $CO_2$ amount to unlabeled $CO_2$ amount, or the ratio of labeled $CO_2$ amount to total $CO_2$ amount in expired air" obtained in step (3-b) (subject value) with "the ratio of labeled $CO_2$ amount to unlabeled $CO_2$ amount, or the ratio of labeled $CO_2$ amount to total $CO_2$ amount in expired air" of healthy subject (control value), thereby determining whether the subject value is lower than the control value.

Regarding steps (3-a) to (3-c), the liver disease test subject, collection of expired air, the ratio of labeled $CO_2$ amount to unlabeled $CO_2$ amount, or the ratio of labeled $CO_2$ amount to total $CO_2$ amount in expired air, the composition, the formulation thereof, labeled C-glucose, components such as arbitrary carriers or additives, the contents of the components, dose, administration method, explanations of target subjects, or executions of the steps are similar to those of steps (1-a) to (1-c), and a person skilled in the art would easily understand steps (3-a) to (3-c) based on the explanations above. Further, accordingly, the composition for energy malnutrition measurement described above may also be referred to as a composition for determining the necessity of nutrition therapy for energy malnutrition.

Further, accordingly, the present invention may also be referred to as providing a step of determining the ratio of labeled $CO_2$ amount to unlabeled $CO_2$ amount, or the ratio of labeled $CO_2$ amount to total $CO_2$ amount in collected expired air (wherein the expired air is expired air that is excreted from the body of a liver disease test subject and contains labeled carbon dioxide generated in the body by being converted from a composition containing, as an active ingredient, glucose labeled with at least one isotope C) (this is referred to as step (3-ab)); or may also be referred to as a method for determining the necessity of nutrition therapy for energy malnutrition, comprising step (3-c) of comparing "the ratio of labeled $CO_2$ amount to unlabeled $CO_2$ amount, or the ratio of labeled $CO_2$ amount to total $CO_2$ amount in expired air" obtained in step (3-ab) (subject value) with "the ratio of labeled $CO_2$ amount to unlabeled $CO_2$ amount, or the ratio of labeled $CO_2$ amount to total $CO_2$ amount in expired air" in healthy subject (control value), thereby determining whether the subject value is lower than the control value.

The present invention enables determination of the necessity of nutrition therapy for energy malnutrition based on the calculation values or the judgments described above. When the subject value is lower than the control value, it is determined that a nutrition therapy for energy malnutrition is necessary; when the subject value is higher than or equivalent to the control value, it is determined that a nutrition therapy for energy malnutrition is unnecessary. Accordingly, the present invention may be considered as determination of the necessity of intervention of nutrition therapy for energy malnutrition.

As described above, the present invention enables easy, rapid, and highly accurate determination of the necessity of a nutrition therapy with respect to a test subject. Based on this determination, it becomes possible to consider or perform an appropriate treatment of the energy malnutrition state. Further, accordingly, the present invention can also be regarded as monitoring of the therapeutic effects or the degree of progression with regard to energy malnutrition state. Further, in the present invention, the determination of the necessity of diet therapy also encompasses determination of diet therapy conditions such as contents of the meals, amounts of the meals, eating time and interval, and the timing of cessation of the therapy.

In the present invention, the test subject may be in a fasting state or non-fasting state immediately before the test is performed, and is preferably in a fasting state. The above explanations may be applied to both a test in a fasting state and a test in a non-fasting state.

Further, as described above, examples of typical treatments of energy malnutrition include a diet therapy, in particular, a therapy with administration of a branched-chain amino acid preparation, or late-evening snacking (LES) in which the patients have a small amount of meal before bedtime so as to avoid energy shortage in the liver at night. On the other hand, in performing such a diet therapy, it is important to perform a diet therapy, in particular, late-evening snacking, in consideration of the presence or absence of a disease, such as diabetes, borderline diabetes, insulin resistance, and the like, that may be worsened in symptom by such a diet therapy.

In this view, in performing a diet therapy, which is a typical treatment of energy malnutrition, it is preferable to know whether the liver disease test subject who was determined to have a subject value lower than the control value has a disease, such as diabetes, borderline diabetes, insulin resistance and the like, that may be worsened in symptom by a diet therapy.

For example, as in the case above, in terms of avoiding the risk of worsening the symptom by a diet therapy, the liver disease test subject who was determined to have a subject value lower than the control value preferably does not have a disease, such as diabetes, borderline diabetes, insulin resistance and the like, that may be worsened in symptom by a diet therapy. To this end, the present invention may further comprise step (3-d) of excluding one or more test subjects having a disease that may be worsened in symptom by a diet therapy for energy malnutrition (at least one disease selected from the group consisting of diabetes, borderline diabetes and insulin resistance) from the liver disease test subjects before step (3-a) or (3-ab), or excluding one or more test subjects having a disease that may be worsened in symptom by a diet therapy for energy malnutrition (for example, at least one disease selected from the group consisting of diabetes, borderline diabetes and insulin resistance) from liver disease test subjects determined to have a subject value lower than the control value in step (3-c). This enables further appropriate determination of the necessity of intervention of nutrition therapy of a liver disease test subject.

Further, the present invention may further comprise step (3-e) of determining whether the liver disease test subject is a test subject having a disease that may be worsened in symptom by a diet therapy for energy malnutrition (at least one disease selected from the group consisting of diabetes, borderline diabetes and insulin resistance) before the exclusion in step (3-d). As in the case above, the determination as to whether the test subject has a disease that may be worsened in symptom by a diet therapy may be performed by any previously known or common diagnosis methods, or based on the standards of the methods.

As is clear from above, the method of the present invention may preferably be applied to a liver disease test subject without a disease, such as diabetes, borderline diabetes, insulin resistance and the like, that may be worsened in symptom by a diet therapy.

Further, the method of the present invention may also preferably be applied to a liver disease test subject having a disease, such as diabetes, that may be worsened in symptom by a diet therapy. An example of this case is more specifically explained below. As in the case above, a test subject having a liver disease, in particular, liver cirrhosis, and diabetes at the same time may have a subject value further lower than the control value, compared with a test subject having only a liver disease. Accordingly, the method of the present invention may also preferably be applied to a liver disease test subject having a liver disease and diabetes at the same time. When the test subject has a subject value further lower than the control value, it is possible to easily and rapidly, and with high accuracy, determine whether a diet therapy for energy malnutrition should be preferentially performed despite the diabetic condition of the test subject. The determination as to whether the liver disease test subject has a disease, such as diabetes, that may be worsened in symptom by a diet therapy may be performed by further performing a step of, as in step (3-e), determining whether the liver disease test subject has a disease that may be worsened in symptom by a diet therapy for energy malnutrition.

As is clear from above, the present invention greatly alleviates the drawbacks of previously known methods for determining energy malnutrition using indirect calorimetry, i.e., for example, the drawbacks such that indirect calorimetry is expensive, requires a special device, can only be performed in limited institutions, can only thus be applied to a limited number of patients, requires complicated operation, requires the patients to be kept quiet in bed and prevented from falling asleep, requires monitoring by an observer, and has an indirect and unclear evaluation. Accordingly, the present invention easily and rapidly determines the necessity of diet therapy for energy malnutrition of a liver disease test subject with high accuracy. Therefore, the execution of the present invention also enables immediate measurement and evaluation with regard to other diseases such as diabetes, borderline diabetes, insulin resistance, and the like, thus enabling easy and rapid determination of the necessity of intervention of nutrition therapy for energy malnutrition with further higher accuracy. In particular, the present invention can be a replacement for the previously known respiratory quotient, and enables determination of the necessity of diet therapy or appropriate diet treatment with regard to energy malnutrition, while excluding diabetes, borderline diabetes, insulin resistance and the like, or while considering the presence of these diseases during a series of diagnoses.

In terms of further reducing constraint and physical or mental pain of the liver disease test subject, in the present invention, for example, for humans, step (3-a) is preferably performed within 120 minutes, more preferably within 1 to 90 minutes after the administration of labeled C-glucose to a liver disease test subject. However, the present invention is not limited to this range. Further, in terms of further rapidly determining the necessity of diet therapy for a liver disease test subject having energy malnutrition, in the present invention, steps (3-a) and (3-b), or step (3-ab) is more preferably performed within 120 minutes, further preferably within 1 to 90 minutes after the administration of labeled C-glucose to a liver disease test subject. However, the present invention is not limited to this range. More preferably, in terms of further rapidly determining the necessity of diet therapy for energy malfunction of a liver disease test subject, steps (3-a), (3-b), and (3-c) or steps (3-ab) and (3-c) are preferably performed within 120 minutes, further preferably within 1 to 90 minutes after the administration of labeled C-glucose to a liver disease test subject. Further, in the present invention, when step (3-d) is performed in addition to these steps, the steps are preferably performed, for example, within 120 minutes, more preferably within 1 to 90 minutes. Further, in the present invention, when step (3-e) is performed in addition to these steps, the steps are preferably performed, for example, within 120 minutes, more preferably within 1 to 90 minutes. The time (required time) is the total time of the times required for the individual steps, i.e., the steps from the administration of labeled C-glucose to a liver disease test subject to the end of the above steps; the steps may be performed either continuously, or non-continuously. For non-humans, a person skilled in the art may set a suitable time by referring to the above range.

As described above, the present invention enables, with high accuracy, easy and rapid judgment as to the necessity of diet therapy for a liver disease test subject having energy malfunction. Therefore, the present invention alleviates or resolves the drawbacks of previously known methods for evaluating energy malnutrition using a means such as indirect calorimetry, for example, the drawbacks such that it is expensive, requires a special device and thus can only be performed in limited institutions, requires complicated operation, has an indirect and unclear evaluation, causes the patients and observers mental or physical pain, and can only be applied to a limited number of patients. Accordingly, the present invention is useful as a replacement for the previously known respiratory quotient. Further, as described above, when it is determined that the liver disease test subject needs a nutrition therapy for an energy malnutrition state, it is possible to consider or perform appropriate diet therapy or treatment for energy malnutrition state based on this determination. Further, when it is determined that a diet therapy for energy malnutrition state is unnecessary, for example, based on this determination, it is determined that the test subject does not particularly need a nutrition therapy for energy malnutrition. Further, accordingly, the present invention can be easily used for monitoring of the therapeutic effects or the degree of progression with regard to energy malnutrition state. Further, in the present invention, the determination of the necessity of diet therapy also encompasses determination of diet therapy conditions such as contents of the meals, amounts of the meals, eating time and interval, and the timing of cessation of the therapy.

Further, since the present invention greatly alleviates the drawbacks of previously known methods for measuring respiratory quotient using indirect calorimetry, it enables easy and rapid comprehension of an energy malnutrition state, as well as the presence or absence of other diseases. Further, even when the liver disease test subject has other diseases such as diabetes, the method of the present invention enables easy, rapid, and highly accurate determination of the necessity of diet therapy for energy malnutrition. Thus, the present invention eases determination of the necessity of intervention of diet therapy for energy malnutrition, as well as enables further appropriate diet therapy for energy malnutrition; therefore, the present invention contributes to improvement in prognosis or quality of life with regard to energy malnutrition.

A palmitic acid breath test is also performed in the Examples, which are described later. The test method, the evaluation method, the composition containing palmitic acid, and the administration of the composition to a test subject in the palmitic acid breath test are substantially the same as those of the labeled-glucose breath test, except that palmitic acid was used instead of glucose. Further, if the control value is higher than the subject value in the palmitic acid breath test, it indicates a decrease in lipid metabolism in the test subject, compared with healthy subject. Further, in addition to palmitic acid, at least one member selected from the group consisting of C12-38 fatty acids or salts thereof may be used.

Examples of C12-38 fatty acids include medium-chain fatty acids having 12 to less than 18 carbon atoms, long-chain fatty acids having 18 to less than 24 carbon atoms, very-long-chain fatty acids having 24 to 28 carbon atoms, and ultra-long-chain fatty acids having 29 to 38 carbon atoms. Preferably, the fatty acid is C12-28 medium-, long-, or very-long-chain fatty acid, more preferably medium- or long-chain fatty acid having 12 to less than 24 carbon atoms. More specifically, examples include lauric acid (C12), myristic acid (C14), pentadecylic acid (C15), palmitic acid (C16), stearic acid (C18), arachidic acid, and like saturated fatty acids; palmitoleic acid (C16), oleic acid (C18), vaccenic acid (C18), nervonic acid (C24), and like unsaturated fatty acids having one double bond; linoleic acid (C18), 8,11-icosadienoic acid, and like unsaturated fatty acids having two double bonds; linolenic acid (C18), arachidonic acid (C20), and like unsaturated fatty acids having three or more double bonds. Preferable examples include saturated fatty acids and unsaturated fatty acids having one double bond; among them, lauric acid (C12), stearic acid (C18), palmitic acid (C16), and oleic acid (C18) are preferable. Stearic acid (C18) and palmitic acid (C16) are particularly preferable.

The salts of these fatty acids may be any pharmaceutically acceptable salts that can be administered to living organisms. Examples thereof include sodium, potassium, or like alkali metal salts; and magnesium, calcium, or like alkaline-earth metal salts. Alkali metal salts are preferable. Sodium salts are particularly preferable.

There is no particular limitation on the isotope to be used in labeling carbon atoms of fatty acid, and specific examples include $^{13}C$ and $^{14}C$. Such isotopes may be radioactive or non-radioactive; however, from the standpoint of safety, non-radioactive isotopes are preferable. For example, $^{13}C$ is desirable for use as such an isotope.

The isotope-labeled fatty acid is labeled in a manner such that at least a portion of the $CO_2$ formed through the lipid metabolic pathway (fatty acid metabolic pathway) is isotope-labeled. Examples of such isotope-labeled fatty acids include compounds in which the carbon atom at 1-position of fatty acid is labeled with an isotope. Specific examples include 1-$^{13}C$-labeled fatty acid. It is sufficient that at least the carbon atom at 1-position of the fatty acid is isotope-labeled; that is, in addition to the carbon atom at 1-position, one or more of other carbon atoms or all of the carbon atoms may be isotope-labeled. There is no particular limitation on the method for labeling compounds such as fatty acid with isotopes such as $^{13}C$ or $^{14}C$, and a wide variety of commonly used methods may be employed, as in the case above. These isotope-labeled fatty acids or salts thereof can be obtained from commercial suppliers. To easily perform the method, these commercially available isotope-labeled fatty acids or salts thereof may be used.

EXAMPLES

The present invention is described below with reference to Examples. However, the present invention is not limited to these Examples.

Reference Example: Measurement of Respiratory Quotient and Energy Consumption (1) Test Method $CCl_4$ (olive oil: $CCl_4$=1:1) was administered subcutaneously to the dorsal regions of male SD rats (10 weeks of age: n=3) in an amount of 2 mL/kg twice a week for 12 weeks, thereby creating liver cirrhosis model rats. With a biogas analysis device (product name: Oxymax, Columbus Instruments), respiratory quotient and energy consumption of untreated rats (control group) and liver cirrhosis model rats (liver cirrhosis model group) were measured and calculated according to the instructions of the device.

Further, both the untreated rats and the liver cirrhosis model rats were fed from 19:00 on Day 1 of the test to 13:00 on Day 3, and were fasted from 13:00 on Day 3 to 13:00 on Day 4, as shown in FIG. 1 shown later. During the non-fasting period, the rats were allowed free access to feed (product name: CRF-1, Oriental Yeast Co., Ltd.). Further, they were in a dark room at night, and in a bright room during the day. According to the difference in liver function or the like, the non-fasting period (daytime) of the rats in this test corresponds to a fasting period of humans.

(2) Test Results

FIG. 1 shows a graph of average values (n=2) of respiratory quotient and energy consumption. The figure shows time transitions of respiratory quotient and energy consumption.

In the control group, the respiratory quotient shifted around the range of 0.9 to 0.95 in the non-fasting period both at night, when rats are active, as well as during the day, when rats are less active. In contrast, in the liver cirrhosis model group, in the non-fasting period, the respiratory quotient shifted in a range lower than that of the control group. In particular, the decrease during the day was significant. In the fasting period, the respiratory quotient was even lower, i.e., the respiratory quotient fell in the range of 0.7 to 0.75 both in the control group and in the liver cirrhosis model group.

The energy consumption increased at night and decreased during the day regardless of whether in the non-fasting period or the fasting period, both in the control group and in the liver cirrhosis model group. Further, the energy consumption amount of the liver cirrhosis model was always lower than that of the control group. As is thus clear, unlike humans, rats are nocturnal animals, and the results regarding energy consumption confirmed that they are active at night (in a high-energy state), and rest during the day (in a low-energy state). Further, it was confirmed that the liver cirrhosis model group has a lower energy state compared with the control group.

Test Example 1: Measurement of Energy Malnutrition by Breath Test (1) Preparation of $^{13}$C-Glucose-Containing Composition U-$^{13}$C-glucose (MW: 186, Cambridge Isotope Laboratories, Inc.) was dissolved in a physiological saline solution at a concentration of 50 μmol/ml, thereby preparing a $^{13}$C-glucose-containing composition.

(2) Preparation of $^{13}$C-Palmitic Acid-Containing Composition

1-$^{13}$C-sodium palmitate (MW: 186, Cambridge Isotope Laboratories, Inc.) was dissolved in hydrous ethanol at about 80° C. at a concentration of 500 μmol/mL. 20% BSA that had been heated to 37° C. was added to the resulting solution and stirred, mixed, and dissolved so that the 1-$^{13}$C-sodium palmitate concentration was 20 μmol/2 ml, thereby preparing a $^{13}$C-palmitic acid-containing composition.

(3) Test Method of Glucose Breath Test

The above-prepared $^{13}$C-glucose-containing composition was individually intravenously administered to the liver cirrhosis model rats and untreated rats prepared in the above Reference Example in an amount of 1 mL/kg (n=3). The administration was performed three times: at 13:00 (A) and 20:00 (B) on Day 1 of the non-fasting period, and at 13:00 (C) in the fasting period. Expired air was collected at time points from before administration (0 minutes) to 120 minutes after the administration of $^{13}$C-glucose-containing composition. $\Delta^{13}$(‰) was measured and determined using an expired air analysis mass spectrometer (ABCA: product of Sercon).

(4) Test Method of Palmitic Acid Breath Test

The above-prepared $^{13}$C-palmitic acid-containing composition was individually intravenously administered to the liver cirrhosis model rats and untreated rats prepared in the above Reference Example in an amount of 2 mL/kg (n=3). The administration was performed twice: at 13:00 (A) on Day 1 of the non-fasting period, and at 13:00 (B) in the fasting period. Expired air was collected at time points between before administration (0 minutes) to 120 minutes after the administration of $^{13}$C-palmitic acid-containing composition. $\Delta^{13}$C(‰) was measured and determined using an expired air analysis mass spectrometer (ABCA: product of Sercon).

(5) Test Results

Figure 2:
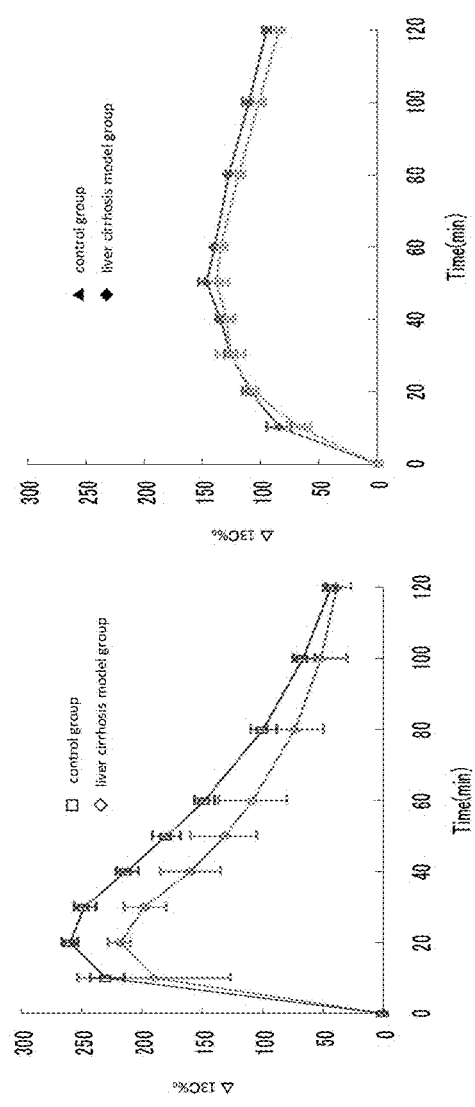
FIGS. 2A, 2B and 2C show results of a labeled C-glucose breath test in a control group and a liver cirrhosis model group.
Figure 2:
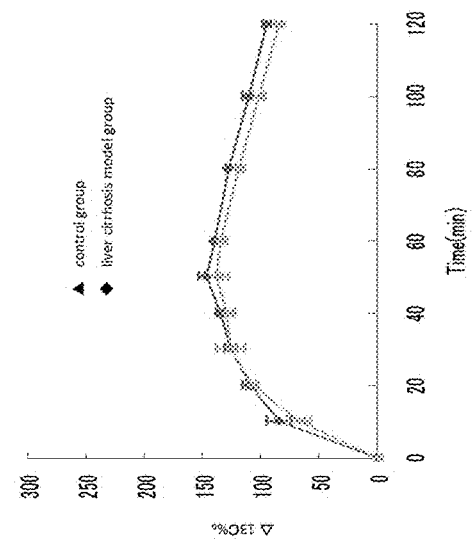
Figure 2:
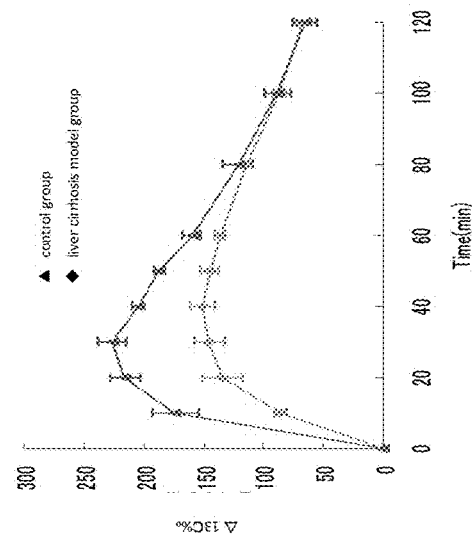

FIGS. 2-A to 2-C show the test results of the glucose breath test. In each graph of these figures, the ordinate axis denotes $\Delta^{13}$C(‰), and the abscissa axis denotes measurement times from before the administration (0 minutes) of $^{13}$C-glucose-containing composition. In the non-fasting period, a significant difference in the expired air reaction ($\Delta^{13}$C(‰)) was not observed between day and night in the control group; however, the expired air reaction significantly decreased during the day in the liver cirrhosis model group. In contrast, in the fasting period, the expired air reaction decreased and showed similar transitions in both groups.

Figure 3:
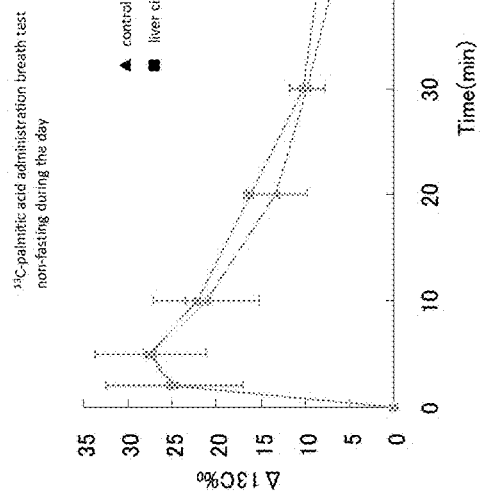
FIGS. 3A and 3B show results of a labeled C-palmitic acid breath test in a control group and a liver cirrhosis model group.
Figure 3:
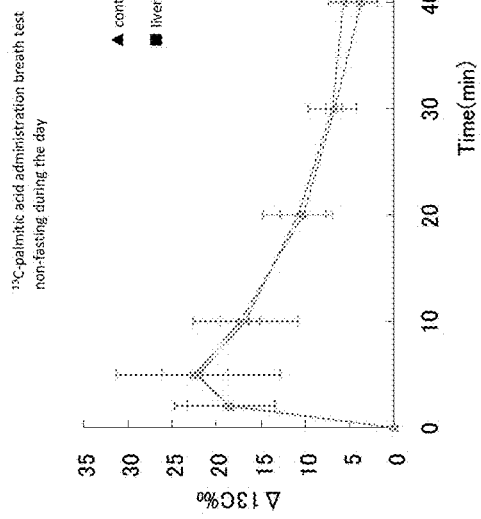

In contrast, FIGS. 3A and 3B show the test results of palmitic acid breath test. In each graph of these figures, the ordinate axis denotes $\Delta^{13}$C(‰), and the abscissa axis denotes measurement times from before the administration (0 minutes) of $^{13}$C-palmitic acid-containing composition. Both in the non-fasting period and the fasting period, the expired air reaction showed similar transitions in the control group and the liver cirrhosis model group.

Test Example 2: Measurement by Breath Test and Correlation with Respiratory Quotient FIG. 4 shows the correlation between respiratory quotient and glucose breath test, based on the results of the Reference Example and Test Example 1.

More specifically, as shown in the Reference Example and Test Example 1, in the control group in the non-fasting period, the respiratory quotient shifted around the range of 0.9 to 0.95 both the day and night; however, in the liver cirrhosis model group in the non-fasting period, the respiratory quotient shifted in a range lower than that of the control group; in particular, the decrease during the day was significant. In contrast, in the fasting period, the respiratory quotient shifted around the range of 0.7 to 0.75 in both of these groups. Also in the glucose breath test, a significant difference was not observed between day and night in the control group in the non-fasting period; however, expired air reaction $\Delta^{13}$C(‰) significantly decreased during the day in the liver cirrhosis model group in the non-fasting period. In the fasting period, the expired air reaction decreased and showed similar transitions in both groups. In contrast, in the palmitic acid breath test, the control group and the liver cirrhosis model group showed similar transitions both in the non-fasting period and the fasting period. Accordingly, the respiratory quotient measured in the Reference Example was compared with the area under the curve ($AUC_{60}$) from 0 minutes to 60 minutes after the $^{13}$C-glucose-containing composition administration calculated from the values obtained in the glucose breath test in Test Example 1. FIG. 4 shows the correlation.

Figure 4:
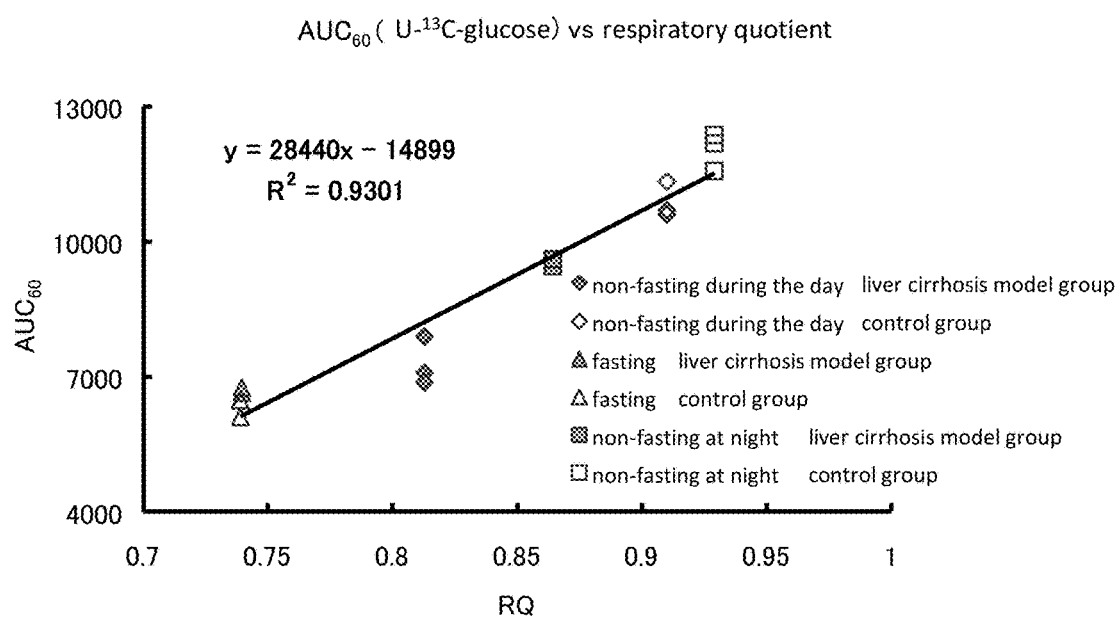
FIG. 4 shows a correlation between respiratory quotient and the results of a labeled C-glucose breath test.

As evident from FIG. 4, a high linearity, i.e., $R_2$=0.9301, was observed between the respiratory quotient and the glucose breath test results, showing a high correlation. Respiratory quotient has previously been used to examine whether a liver cirrhosis patient is in an energy malnutrition state. The above results show that the determination as to whether a liver cirrhosis patient is in an energy malnutrition state may also be performed by using a glucose breath test. In particular, the respiratory quotient measurement has drawbacks such that it is expensive, requires a special device, can only be performed in limited institutions, can only thus be applied to a limited number of patients, requires complicated operation, requires the patients to be kept quiet in bed and prevented from falling asleep, requires monitoring by an observer, and has an indirect and unclear evaluation; however, it was revealed that it is possible to easily and rapidly find an energy malnutrition state of a liver cirrhosis patient while greatly alleviating the drawbacks such as physical pain and ensuring a high correlation with respiratory quotient by using a glucose breath test. It was further revealed that, by thus directly and accurately finding a glucose metabolism degree, i.e., an energy malnutrition state, by using a glucose breath test, more appropriate diet therapies or the like for energy malnutrition can be planned and performed.

Further, from the results of respiratory quotient in the non-fasting period, it was predicted that, although sugar was used as an energy source in the control group, lipid was mainly used as an energy source in the liver cirrhosis model group. However, as shown in Test Example 1, since an increase in lipid metabolism was not confirmed in the palmitic acid breath test, it was assumed that the low values of respiratory quotient in the liver cirrhosis model group is derived from a decrease in glucose metabolism. Further, as described above, since high correlation was confirmed between respiratory quotient and glucose breath test, it was confirmed that, by using the glucose breath test instead of the previously known respiratory quotient, it is possible to easily, rapidly, and highly accurately determine an energy malnutrition state of a liver disease patient while greatly alleviating the drawbacks of the previously known respiratory quotient calculation.

The invention claimed is:

1. A method for determining the necessity of a nutrition therapy for a liver disease test subject having energy malnutrition, comprising steps (A), (B) and (C) below:
(A) administering, to a liver disease test subject, a composition containing, as an active ingredient, glucose labeled with at least one isotope C that is converted in the body into labeled carbon dioxide and excreted in expired air, in an effective amount for determining the necessity of a nutrition therapy for the liver disease test subject having energy malnutrition, and collecting the expired air,
(B) determining the ratio of labeled $CO_2$ amount to unlabeled $CO_2$ amount, or the ratio of labeled $CO_2$ amount to total $CO_2$ amount in the collected expired air; and
(C) comparing "the ratio of labeled $CO_2$ amount to unlabeled $CO_2$ amount, or the ratio of labeled $CO_2$ amount to total $CO_2$ amount in the expired air" (subject value) obtained in step (B) with "the ratio of labeled $CO_2$ amount to unlabeled $CO_2$ amount, or the ratio of labeled $CO_2$ amount to total $CO_2$ amount in the expired air" in healthy subject (control value), thereby determining whether the subject value is lower than the control value.

2. The method according to claim 1, further comprising step (C) (D) below:
(D) excluding one or more test subjects having a disease that may be worsened in symptom by a diet therapy for energy malnutrition from liver disease test subjects before step (B), or excluding one or more test subjects having a disease that may be worsened in symptom by a diet therapy for energy malnutrition from liver disease test subjects determined to have a subject value lower than the control value in step (C).

3. The method according to claim 2, further comprising step (E) below:
(E) determining whether the liver disease test subject has a disease that may be worsened in symptom by a diet therapy for energy malnutrition before the exclusion in step (D).

4. The method according to claim 1, wherein the liver disease test subject is a liver cirrhosis test subject.

5. The method according to claim 1, wherein the liver disease test subject also has diabetes.

6. The method according to claim 1, wherein the expired air is collected from a liver disease test subject in a fasting state.

7. The method according to claim 1, wherein the isotope C is $^{13}$C.

8. A method for measuring energy malnutrition in a liver disease test subject, comprising steps (A') and (B') below:
(A') administering, to a liver disease test subject, a composition containing, as an active ingredient, glucose labeled with at least one isotope C that is converted in the body into labeled carbon dioxide and excreted in expired air, in an effective amount for measuring energy malnutrition in the liver disease test subject, and collecting the expired air; and
(B') determining the ratio of labeled $CO_2$ amount to unlabeled $CO_2$ amount, or the ratio of labeled $CO_2$ amount to total $CO_2$ amount in the collected expired air.

9. The method according to claim 8, further comprising step (C') below:
(C') comparing "the ratio of labeled $CO_2$ amount to unlabeled $CO_2$ amount, or the ratio of labeled $CO_2$ amount to total $CO_2$ amount in the expired air" (subject value) with "the ratio of labeled $CO_2$ amount to unlabeled $CO_2$ amount, or the ratio of labeled $CO_2$ amount to total $CO_2$ amount in the expired air" in healthy subject (control value), thereby determining whether the subject value is lower than the control value.

10. The method according to claim 8, wherein the liver disease test subject is a liver cirrhosis test subject.

11. The method according to claim 8, wherein the liver disease test subject does not have a disease that may be worsened in symptom by a diet therapy for energy malnutrition.

12. The method according to claim 8, wherein the liver disease test subject also has diabetes.

13. The method according to claim 8, wherein the expired air is collected from a liver disease test subject in a fasting state.

14. A method for determining whether a liver disease test subject is in an energy malnutrition state, comprising steps (A") and (B") below:
(A") administering, to a liver disease test subject, a composition containing, as an active ingredient, glucose labeled with at least one isotope C that is converted in the body into labeled carbon dioxide and excreted in expired air, in an effective amount for determining whether the liver disease test subject is in an energy malnutrition state, and collecting the expired air; and (B") determining the ratio of labeled $CO_2$ amount to unlabeled $CO_2$ amount, or the ratio of labeled $CO_2$ amount to total $CO_2$ amount in the expired air.

15. The method according to claim 14, further comprising step (C") below:

(C") comparing "the ratio of labeled $CO_2$ amount to unlabeled $CO_2$ amount, or the ratio of labeled $CO_2$ amount to total $CO_2$ amount in the expired air" in the test subject (subject value) obtained in step (B") with "the ratio of labeled $CO_2$ amount to unlabeled $CO_2$ amount, or the ratio of labeled $CO_2$ amount to total $CO_2$ amount in the expired air" in healthy subject (control value), and determining that the test subject is in an energy malnutrition state when the subject value is lower than the control value, and determining that the test subject is not in an energy malnutrition state when the subject value is equal to or higher than the control value.

16. The method according to claim 14, further comprising step (D") below:

(D") excluding one or more test subjects having a disease that may be worsened in symptom by a diet therapy for energy malnutrition from liver disease test subjects before step (A"), or excluding one or more test subjects having a disease that may be worsened in symptom by a diet therapy for energy malnutrition from liver disease test subjects determined to have an energy malnutrition state in step (C").

17. The method according to claim 16, further comprising step (E") below:

(E") determining whether the liver disease test subject is a test subject having a disease that may be worsened in symptom by a diet therapy for energy malnutrition before the exclusion in step (D").

18. The method according to claim 14, wherein the liver disease test subject is a liver cirrhosis test subject.

19. The method according to claim 14, wherein the liver disease test subject also has diabetes.

20. The method according to claim 14, wherein step (A") is performed with a liver disease test subject in a fasting state.

21. The method according to claim 1, further comprising step (F), (F) determining the necessity of a nutrition therapy for the liver disease test subject when the subject value is lower than the control value.

* * * * *

UNITED STATES PATENT AND TRADEMARK OFFICE
CERTIFICATE OF CORRECTION

PATENT NO. : 10,393,730 B2
APPLICATION NO. : 15/324486
DATED : August 27, 2019
INVENTOR(S) : Makoto Inada, Jun-ichi Kunizaki and Kazuki Tobita It is certified that error appears in the above-identified patent and that said Letters Patent is hereby corrected as shown below:

In the Claims

Claim 2, Column 30, Line 6; Delete "(C)" after "step"

Signed and Sealed this
Nineteenth Day of November, 2019

Andrei Iancu
*Director of the United States Patent and Trademark Office*